United States Patent
Tanahashi et al.

(10) Patent No.: US 10,131,555 B2
(45) Date of Patent: Nov. 20, 2018

(54) METHOD AND APPARATUS FOR CONTROLLING CONCENTRATION OF FREE CHLORINE, AND STERILIZATION METHOD AND STERILIZATION APPARATUS EACH UTILIZING SAID METHOD AND SAID APPARATUS

(71) Applicants: NIKKISO CO., LTD., Tokyo (JP); TANAH PROCESS, LTD., Osaka-shi, Osaka (JP)

(72) Inventors: Masakazu Tanahashi, Osaka (JP); Junichi Watanabe, Osaka (JP); Masato Fujiwara, Higashimurayama (JP); Rongfu Lu, Makinohara (JP)

(73) Assignees: NIKKISO CO., LTD., Tokyo (JP); TANAH PROCESS, LTD., Osaka-shi (JP)

( * ) Notice: Subject to any disclaimer, the term of this patent is extended or adjusted under 35 U.S.C. 154(b) by 240 days.

(21) Appl. No.: 15/116,114

(22) PCT Filed: Jan. 30, 2015

(86) PCT No.: PCT/JP2015/052728
§ 371 (c)(1),
(2) Date: Aug. 2, 2016

(87) PCT Pub. No.: WO2015/119059
PCT Pub. Date: Aug. 13, 2015

(65) Prior Publication Data
US 2017/0137305 A1    May 18, 2017

(30) Foreign Application Priority Data

Feb. 6, 2014 (JP) .................................. 2014-020876
Jan. 13, 2015 (JP) .................................. 2015-003886

(51) Int. Cl.
C02F 1/46 (2006.01)
C02F 1/467 (2006.01)
(Continued)

(52) U.S. Cl.
CPC .............. C02F 1/4674 (2013.01); A61L 2/18 (2013.01); C25B 1/26 (2013.01); C25B 15/02 (2013.01);
(Continued)

(58) Field of Classification Search
None
See application file for complete search history.

(56) References Cited

U.S. PATENT DOCUMENTS

| 4,127,458 A | 11/1978 | MacGregor |
| 5,256,268 A | 10/1993 | Goto et al. |

(Continued)

FOREIGN PATENT DOCUMENTS

| EP | 1340847 A1 | 9/2003 |
| EP | 1903128 A2 | 3/2008 |

(Continued)

OTHER PUBLICATIONS

Jan. 25, 2017 Extended European Search Report issued in Patent Application No. 15745808.4.
(Continued)

*Primary Examiner* — Arun S Phasge
(74) *Attorney, Agent, or Firm* — Oliff PLC

(57) ABSTRACT

The method includes a process of (i) and a process of (ii) in this order. In the process of (i), the potential of a first anode and the potential of a first cathode are adjusted in an aqueous solution containing chloride ions so as to increase the concentration of free chlorine in the aqueous solution. In the process of (ii), the potential of a second anode and the potential of a second cathode are adjusted in the aqueous
(Continued)

solution so as to decrease the concentration of free chlorine in the aqueous solution. The difference between the potential of the second anode and the potential of the second cathode in the process of (ii) is smaller than the difference between the potential of the first anode and the potential of the first cathode in the process of (i).

20 Claims, 20 Drawing Sheets

(51) Int. Cl.
    *A61L 2/18*     (2006.01)
    *C25B 1/26*     (2006.01)
    *C25B 15/02*     (2006.01)

(52) U.S. Cl.
    CPC . *A61L 2202/11* (2013.01); *C02F 2201/46135* (2013.01); *C02F 2209/06* (2013.01); *C02F 2209/29* (2013.01); *C02F 2209/40* (2013.01)

(56) References Cited

U.S. PATENT DOCUMENTS 6,106,691 A      8/2000      Nakamura et al.
2009/0173635 A1*      7/2009      Tongiani .................. C02F 1/467
                                                                                                                                                                                 205/335
2013/0125316 A1      5/2013      Bhuta et al.

FOREIGN PATENT DOCUMENTS

| | | |
|---|---|---|
| JP | H04-78486 A | 3/1992 |
| JP | H05-179475 A | 7/1993 |
| JP | H06-153744 A | 6/1994 |
| JP | H11-226092 A | 8/1999 |
| JP | H11-290855 A | 10/1999 |
| JP | 2004-223419 A | 8/2004 |
| JP | 2005-060761 A | 3/2005 |
| JP | 2006-239531 A | 9/2006 |
| JP | 2007-117882 A | 5/2007 |
| WO | 2008/105613 A1 | 9/2008 |
| WO | 2010/027825 A2 | 3/2010 |

OTHER PUBLICATIONS

Aug. 18, 2016 International Preliminary Report on Patentability issued in Patent Application No. PCT/JP2015/052728.

Mar. 10, 2015 International Search Report issued in Patent Application No. PCT/JP2015/052728.

Jul. 24, 2018 Office Action issued in Japanese Application No. 2015-003886.

* cited by examiner

METHOD AND APPARATUS FOR CONTROLLING CONCENTRATION OF FREE CHLORINE, AND STERILIZATION METHOD AND STERILIZATION APPARATUS EACH UTILIZING SAID METHOD AND SAID APPARATUS

TECHNICAL FIELD

The present invention relates to a method and an apparatus for controlling the concentration of free chlorine, and also relates to a sterilization method and a sterilization apparatus which utilize said method and apparatus.

BACKGROUND ART

Methods for performing sterilization by producing hypochlorite from salt water have already been proposed. For example, a method for producing hypochlorite by electrolysis using a cation exchange membrane has been proposed (Patent Document 1).

When sterilization is performed using hypochlorite, it is sometimes preferable to remove the residual hypochlorite after the sterilization. As a result, methods for removing hypochlorite have been proposed. For example, a method has been proposed in which a water for treatment containing an available chlorine component is supplied to a single-electrode electrolytic cell, and the available chlorine component is decomposed or reduced at the cathode (Patent Document 2). Patent Document 2 discloses the use of a carbon-based material as the cathode material, and discloses that the application of a low voltage which is accompanied by substantially no gas generation is preferable.

Further, a method in which the production and decomposition of hypochlorite are achieved by application of a voltage has also been proposed (Patent Document 3). Patent Document 3 discloses that by using a pair of AC electrodes and two prescribed ground electrodes, the generation and reduction of sodium hypochlorite is possible.

The method of Patent Document 1 requires the use of a cation exchange membrane, and therefore regeneration of the cation exchange membrane is necessary, control of the apparatus is complex, and the maintenance costs tend to increase. Further, Patent Document 2 discloses only a method for reducing the concentration of free chlorine. Furthermore, Patent Document 3 includes no indication of the size of the effect actually achieved using the method of Patent Document 3, and therefore the effectiveness of the method of Patent Document 3 is unclear.

CITATION LIST

Patent Literature

Patent Document 1: JP H05-179475 A
Patent Document 2: JP H04-78486 A
Patent Document 3: JP 2006-239531 A

SUMMARY OF INVENTION

Technical Problem

In light of these circumstances, one object of the present invention is to provide a novel method that can easily control the concentration of free chlorine, a sterilization method that utilizes this method, and a novel apparatus that can easily control the concentration of free chlorine.

Solution to Problem

As a result of investigations aimed at achieving the above object, the inventors of the present invention discovered a phenomenon not previously known. The present invention is based on this novel finding.

The present invention provides a method for controlling the concentration of free chlorine. This method is a method of controlling the concentration of free chlorine using a plurality of electrodes, the method comprising, in order, (i) adjusting the potential of a first anode and the potential of a first cathode in an aqueous solution containing chloride ions, thereby increasing the concentration of free chlorine in the aqueous solution, and (ii) adjusting the potential of a second anode and the potential of a second cathode in the aqueous solution, thereby decreasing the concentration of free chlorine in the aqueous solution, wherein the difference between the potential of the second anode and the potential of the second cathode in a process of (ii) is smaller than the difference between the potential of the first anode and the potential of the first cathode in a process of (i), the first anode and the first cathode are composed of one portion and one other portion of the plurality of electrodes, respectively, and the second anode and the second cathode are composed of one portion and one other portion of the plurality of electrodes, respectively.

Further, the present invention provides a sterilization method. This sterilization method performs sterilization using an aqueous solution containing free chlorine, and includes the method of the present invention for controlling the concentration of free chlorine, the sterilization method comprising (I) sterilizing a sterilization target using the aqueous solution treated by the aforementioned process of (i).

Furthermore, the present invention provides an apparatus. This apparatus controls the concentration of free chlorine, and includes a plurality of electrodes, a power source for applying a voltage to the plurality of electrodes, and a controller for controlling the power source, wherein the controller executes the aforementioned processes of (i) and (ii) in that order, the difference between the potential of the second anode and the potential of the second cathode in the process of (ii) is smaller than the difference between the potential of the first anode and the potential of the first cathode in the process of (i), the first anode and the first cathode are composed of one portion and one other portion of the plurality of electrodes, respectively, and the second anode and the second cathode are composed of one portion and one other portion of the plurality of electrodes, respectively.

Moreover, the present invention provides a sterilization apparatus. This sterilization apparatus performs sterilization using an aqueous solution containing free chlorine, and includes the apparatus of the present invention for controlling the concentration of free chlorine, wherein the controller executes (I) sterilizing a sterilization target using the aqueous solution treated by the aforementioned process of (i).

Advantageous Effects of the Invention

By using the methods and apparatus of the present invention, the concentration of free chlorine in an aqueous solution can be controlled easily. Further, in the sterilization method and sterilization apparatus of the present invention, a sterilization target can be sterilized using an aqueous solution having an increased concentration of free chlorine.

DESCRIPTION OF EMBODIMENTS

Figure 1:
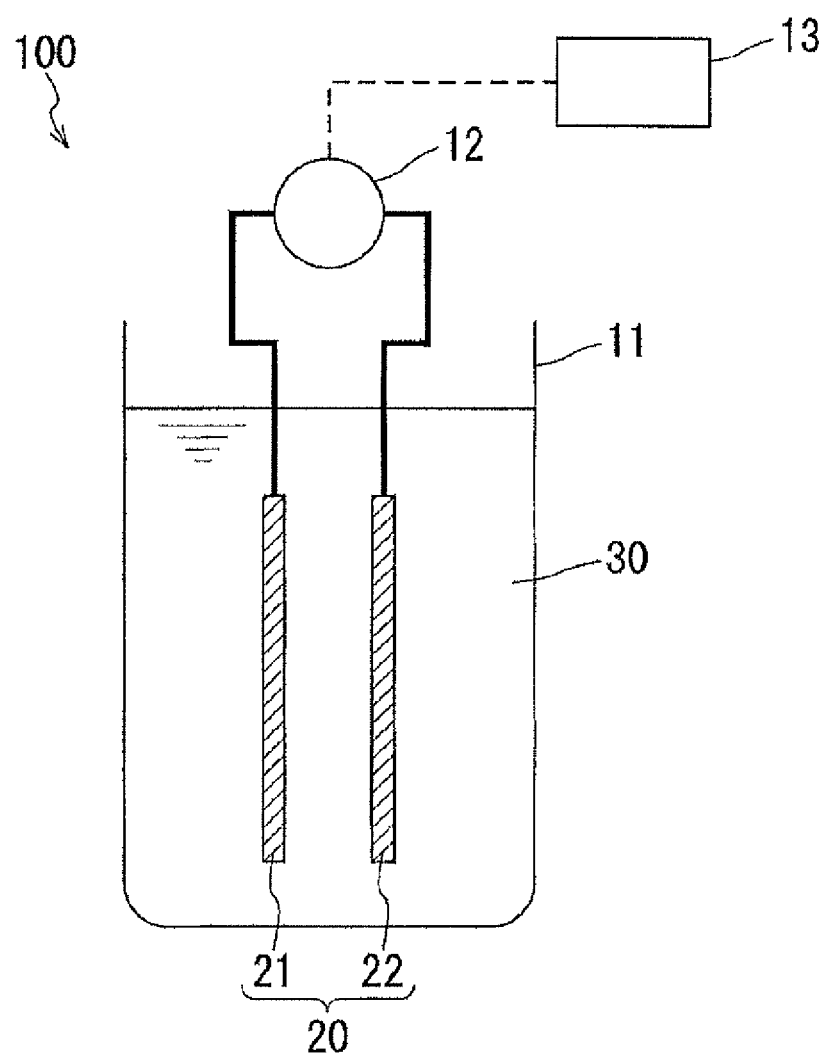
FIG. 1 is a schematic view illustrating one example of an apparatus of the present invention.

Embodiments of the present invention are described below. In the following description, examples of embodiments of the present invention are described, but the present invention is not limited to the examples described below. In the following description, specific numerical values and materials are sometimes presented as examples, but other numerical values and materials may also be employed, provided that the effects of the present invention can be obtained. In descriptions using the drawings, identical portions are labeled with the same reference signs, and duplicate descriptions may sometimes be omitted.

(Method for Controlling Concentration of Free Chlorine)

One example of the method of the present invention for controlling the concentration of free chlorine (the available chlorine concentration) is described below. In this method, a plurality of electrodes are used to control the concentration of free chlorine. This method includes a process of (i) and a process of (ii) described below in that order. The plurality of electrodes is typically composed of two electrodes that constitute one electrode pair. However, the present invention may also include other electrodes besides those two electrodes.

In process (i), the potentials of two electrodes selected from the plurality of electrodes are adjusted so that the two electrodes function as an anode and a cathode in an aqueous solution containing chloride ions, thereby increasing the concentration of free chlorine in the aqueous solution. In the following description, the aqueous solution treated by processes (i) and (ii) is sometimes termed "the aqueous solution (S)". Further, the anode and the cathode in process (i) are sometimes termed "the first anode" and "the first cathode" respectively.

From another viewpoint, in process (i), the potential of the first anode and the potential of the first cathode in the aqueous solution (S) comprising chloride ions are adjusted, thereby increasing the concentration of free chlorine in the aqueous solution (S). The first anode and the first cathode are composed of one portion and one other portion of the plurality of electrodes, respectively. The plurality of electrodes may also include an electrode that constitutes neither the first anode nor the first cathode.

Examples of the adjustment of the potentials of the two electrodes include those cases in which the potential difference between the two electrodes is adjusted, and include, for example, the case in which the potential difference between the two electrodes is adjusted by applying a DC voltage between the two electrodes (this also applies in process (ii)). In other words, in one example of process (i), a DC voltage is applied between the first anode and the first cathode, and the potentials of the electrodes are adjusted only by that voltage application.

In process (i), chloride ions are oxidized and chlorine molecules are produced at the surface of the anode. These chlorine molecules react with the water to produce hypochlorous acid and hypochlorite ions. In other words, the voltage application in process (i) increases the concentration of free chlorine (dissolved chlorine, hypochlorous acid and hypochlorite ions).

The aqueous solution (S) contains chloride ions. One preferred example of the aqueous solution (S) is water containing a dissolved metal chloride such as an alkali metal chloride. Examples of alkali metal chlorides include sodium chloride (NaCl) and potassium chloride (KCl). One example of the aqueous solution (S) is an aqueous solution in which is dissolved at least one compound selected from among sodium chloride and potassium chloride, and the aqueous solution (S) may be a sodium chloride aqueous solution. Further, other examples of the aqueous solution (S) include physiological saline solution (a sodium chloride aqueous solution) and liquids used in blood treatment apparatus (such as the dialysis fluid used in an artificial dialysis apparatus). The main component of dialysis fluid is sodium chloride, and the concentration of the sodium chloride is about 0.7 wt %. Other examples of the aqueous solution (S) include tap water and ground water.

If the chloride ion concentration is too low, then in process (i), the concentration of free chlorine may not be able to be increased sufficiently, or the voltage drop in the aqueous solution (S) may become too large. On the other hand, if the chloride ion concentration is too high, then the time required to reduce the concentration of free chlorine in process (ii) described below may sometimes lengthen. Accordingly, the chloride ion concentration in the aqueous solution (S) is preferably within a suitable range. The chloride ion concentration in the aqueous solution (S) may be within a range from 17 mmol/L to 582 mmol/L. The concentration of a sodium chloride aqueous solution (molar mass of sodium chloride: 58.4 g/mol) that yields a chloride ion concentration of 17 mmol/L is about 0.1 wt % (0.017× 58.4×100/1000). The concentration of a sodium chloride aqueous solution that yields a chloride ion concentration of 582 mmol/L is about 3.4 wt % (0.582×58.4×100/1000). When the aqueous solution (S) is an aqueous solution of an alkali metal chloride (for example, sodium chloride and/or potassium chloride), the concentration may fall within a range from 0.7 wt % to 7.2 wt %.

In process (ii), the potentials of two electrodes selected from the plurality of electrodes are adjusted so that the two electrodes function as an anode and a cathode in the aqueous solution (S), thereby decreasing the concentration of free chlorine in the aqueous solution (S). In the following description, the anode and the cathode in the voltage application of process (ii) are sometimes termed "the second anode" and "the second cathode" respectively.

From another viewpoint, in process (ii), the potential of the second anode and the potential of the second cathode in the aqueous solution (S) are adjusted, thereby decreasing the concentration of free chlorine in the aqueous solution (S). The second anode and the second cathode are composed of one portion and one other portion of the plurality of electrodes, respectively. The plurality of electrodes may also include an electrode that constitutes neither the second anode nor the second cathode.

In the method of the present invention, the potential difference between the two electrodes in process (ii) (the difference between the potential of the second anode and the potential of the second cathode) is set to a value smaller than the potential difference between the two electrodes in process (i) (the difference between the potential of the first anode and the potential of the first cathode).

In process (ii), the free chlorine component is decomposed at the surface of the second cathode, resulting in a reduction in the concentration of free chlorine in the aqueous solution (S). Accordingly, by increasing the surface area of the second cathode, the amount of free chlorine can be reduced efficiently. For example, the surface area of the second cathode in process (ii) may be larger than the surface area of the second anode in process (ii). By making the surface area of the second cathode larger than the surface area of the second anode, the overall electrode size can be reduced and the rate of reduction in the concentration of free chlorine can be increased.

The surface area of the second cathode may be larger than the surface area of the second anode. In one example, the surface area of the second cathode is larger than the surface area of the first cathode, and the surface area of the second cathode is also larger than the surface area of the second anode. In other words, the surface area of the second cathode may be larger than both the surface area of the first cathode and the surface area of the second anode. The surface area of the second cathode may be at least twice, or at least 3 times, the surface area of the second anode, and may be not more than 20 times, or not more than 12 times, or not more than 9 times, the surface area of the second anode. For example, the surface area of the second cathode may be within a range from 2 to 12 times, or within a range from 3 to 12 times, or within a range from 3 to 9 times, the surface area of the second anode.

In one example, the conditions (1) and (2) described below may be satisfied, and the condition (3) may also be satisfied.
(1) The surface area of the first cathode is within a range from 0.5 to 2 times the surface area of the first anode.
(2) The surface area of the second cathode is within a range from 2 to 12 times, or within a range from 3 to 12 times, or within a range from 3 to 9 times, the surface area of the second anode.
(3) The surface area of the first anode is within a range from 0.5 to 2 times the surface area of the second anode.

In one example, the plurality of electrodes may include a first electrode used as the first anode, a second electrode used as the first cathode, and a third electrode. In this example, a voltage need not be applied to the third electrode in process (i), and the third electrode may be used as at least a portion of the second cathode in process (ii). For example, in process (ii), the first electrode may be used as the second anode, and the second and third electrodes may be used as the second cathode. In one preferred example, the surface area of the third electrode is set within a range from 2 to 11 times the surface area of the first electrode, and the surface area of the third electrode is set within a range from 2 to 11 times the surface area of the second electrode. An example using the third electrode is described in Example 7.

In process (i), the potentials of the electrodes are adjusted so that the concentration of free chlorine increases. In contrast, in process (ii), the potentials of the electrodes are adjusted so that the concentration of free chlorine decreases. The potentials that cause the concentration of free chlorine to increase and decrease may vary depending on the solute and concentration of the aqueous solution (S), and the material of the electrodes. Accordingly, the potentials are preferably adjusted with due consideration of these factors.

In those cases where the potentials are adjusted by controlling the magnitude of the DC voltage applied between the anode and the cathode, a DC voltage that causes an increase in the concentration of free chlorine is applied in process (i), and a DC voltage that causes a decrease in the concentration of free chlorine is applied in process (ii). In such cases, the magnitude of the DC voltage applied between the electrodes in process (ii) is set to a smaller value than the magnitude of the DC voltage applied between the electrodes in process (i).

There are no particular limitations on the shapes of the anodes and cathodes used in process (i) and process (ii). The electrodes may be plate-like electrodes, or some other shape. From the viewpoint of accelerating the reaction at the electrode surface, an electrode having a large surface area may be used, or an electrode may be used which has passages formed therein through which the aqueous solution (S) can pass. For example, an electrode formed by grouping a series of metal wires (such as a net-like electrode), or a porous electrode may be used. Furthermore, an electrode having through-holes formed therein, such as an electrode that uses a punched metal or an expanded metal, may also be used.

Figure 4:
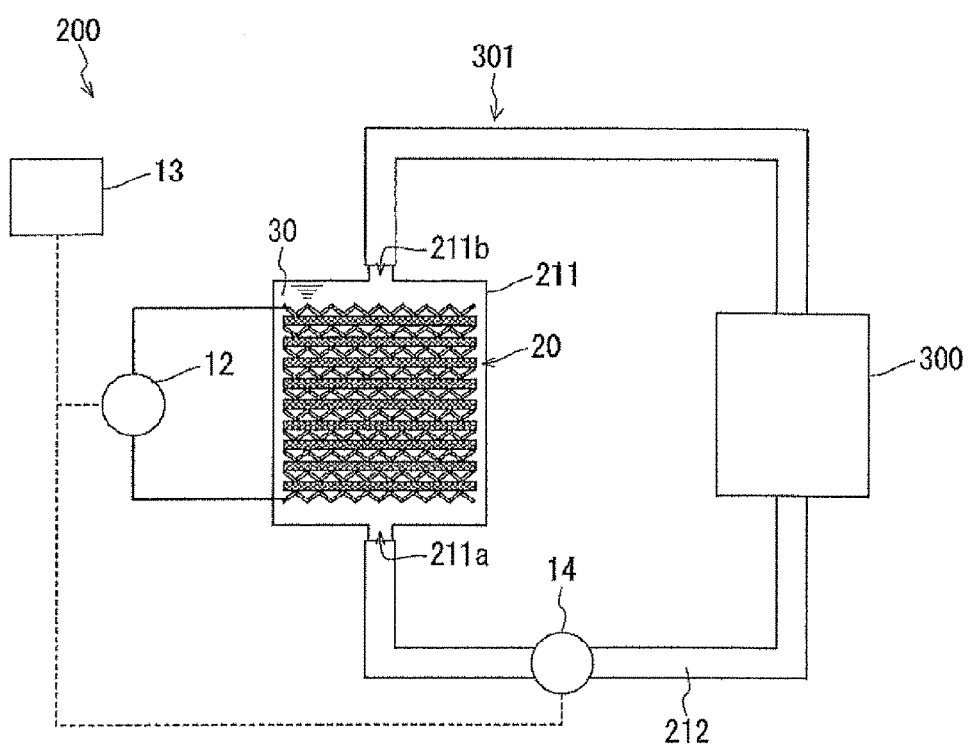
FIG. 4 is a schematic view illustrating another example of an apparatus of the present invention.
Figure 15:
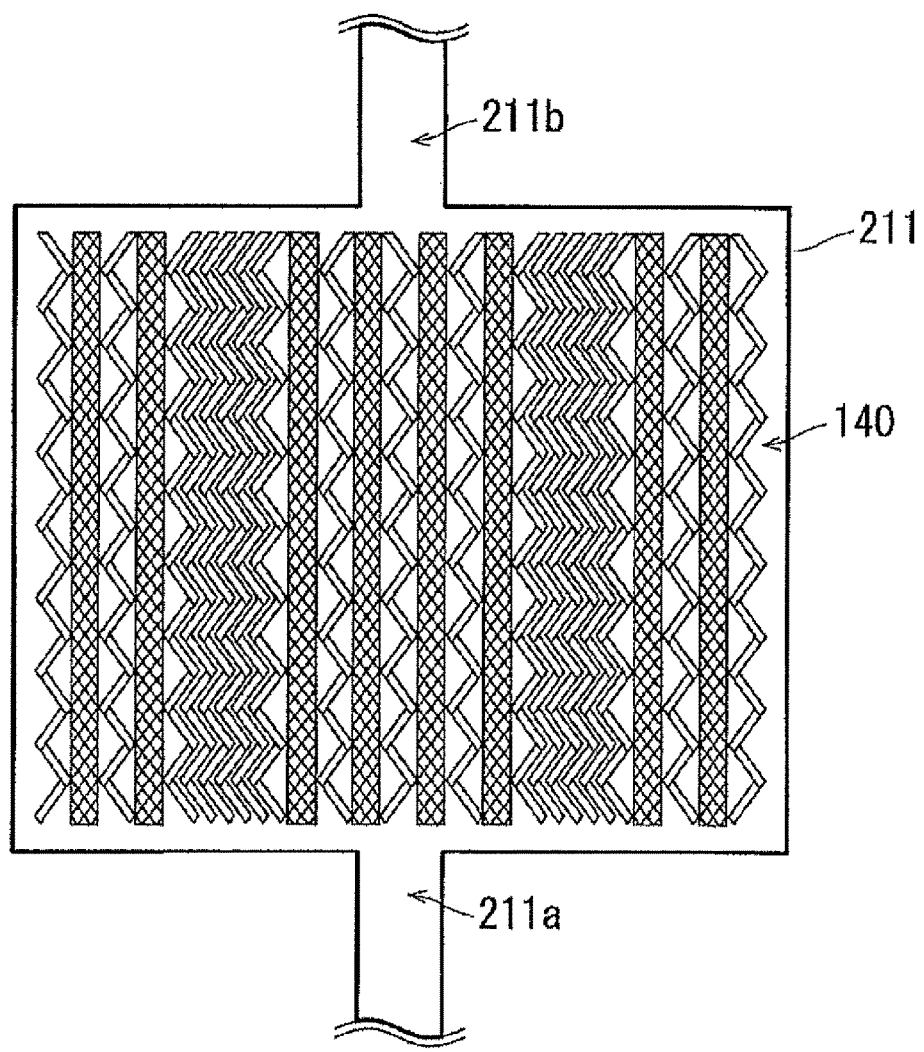
FIG. 15 is a diagram schematically illustrating the structure of one example of an electrolytic cell used in Example 7.

The anode and the cathode may each be an electrode having a shape that extends in two dimensions. For example, the anode and the cathode may each be a flat plate electrode having through-holes formed therein, or may be a net-like electrode. As illustrated in FIG. 4, these types of flat electrodes may be positioned so that the in-plane direction of the electrodes is arranged orthogonally relative to the flow direction of the aqueous solution (S). Alternatively, as illustrated in FIG. 15, the electrodes may be arranged so that the in-plane direction of the electrodes is parallel to the flow direction of the aqueous solution (S).

In the present invention, the plurality of electrodes may be composed of two electrodes. In this description, in those cases where a plurality of electrodes that are connected by wiring or the like and are at substantially the same potential function as a single anode or a single cathode, that plurality of electrodes is counted as a single electrode.

The two electrodes for which the potentials are adjusted in process (i) (the first anode and the first cathode) may be used as the two electrodes for which the potentials are adjusted in process (ii) (the second anode and the second cathode). For example, the anode and the cathode in process (i) may be used as the anode and the cathode respectively in process (ii). In other words, voltages may be applied in process (i) and process (ii) without altering the anode or the cathode (without altering the direction of voltage application). Further, the anode and the cathode in process (i) may be used as the cathode and the anode respectively in process (ii). In other words, in process (ii), the voltage may be applied in the reverse direction to that used in process (i). Furthermore, at least one of the anode and the cathode in process (ii) may be a different electrode from either the anode or the cathode in process (i).

In one example of the present invention, a DC voltage is applied between the two electrodes (the first anode and the first cathode) for which the potentials are to be adjusted in process (i), thereby adjusting the potentials of the two electrodes, and a DC voltage is then applied between the two electrodes (the second anode and the second cathode) for which the potentials are to be adjusted in process (ii), thereby adjusting the potentials of those two electrodes.

One example of a preferred electrode is an electrode in which platinum exists at the surface. In the following description, an electrode in which platinum exists at the surface (for example, an electrode having a surface coated with platinum) is sometimes termed a "platinum-coated electrode". A platinum-coated electrode can be used favorably as the anode of process (ii). All of the plurality of electrodes may be platinum-coated electrodes. Other examples of the electrode include electrodes in which iridium oxide exists at the surface (for example, an electrode having a surface coated with iridium oxide). In the following description, an electrode in which iridium oxide exists at the surface is sometimes termed an "iridium oxide-coated electrode".

In process (ii) in which the concentration of free chlorine is reduced, the use of a platinum-coated electrode as the anode is preferable. Further, in process (i) in which the concentration of free chlorine is increased, the use of an iridium oxide-coated electrode as the anode is preferable. In one example of the present invention, a platinum-coated electrode and an iridium oxide-coated electrode may be used as the plurality of electrodes. In this example, in process (i), a DC voltage is applied between the two electrodes with the iridium oxide-coated electrode used as the anode and the platinum-coated electrode used as the cathode, whereas in process (ii), a DC voltage is applied between the two electrodes with the platinum-coated electrode used as the anode and the iridium oxide-coated electrode used as the cathode. By employing this configuration, the concentration of free chlorine can be increased efficiently in process (i), and the concentration of free chlorine can be reduced efficiently in process (ii).

A spacer may be disposed between the electrodes. One of the purposes of providing a spacer is to prevent short-circuits between the anode and the cathode. Further, providing a spacer facilitates the flow of the aqueous solution (S) between the electrodes. An insulating spacer may be used as the spacer, and for example, a resin spacer may be used. One example of a preferred spacer is a net-like resin spacer.

Each of process (i) and process (ii) may, independently, be conducted using a batch method or a flow method. In the batch method, the aqueous solution (S) inside the electrolytic cell in which the anode and the cathode are disposed undergoes substantially no movement during each process. In contrast, in the flow method, the aqueous solution (S) is moved between the electrolytic cell and a region outside the electrolytic cell during each process. In a typical flow method, the aqueous solution (S) flows continuously through the electrolytic cell.

The difference between the potential of the first anode and the potential of the first cathode in process (i) may be at least 4 V, at least 5 V, or 7 V or more, and may be not more than 60 V, not more than 20 V, or 12 V or less. The difference between the potential of the second anode and the potential of the second cathode in process (ii) may be less than 4 V, 3 V or less, or 2 V or less, and may be at least 0.6 V or 1.2 V or more.

In one example, a DC voltage of at least 4 V (for example, a voltage within a range from 4 V to 12 V or within a range from 5 V to 12 V) is applied between the first anode and the first cathode in process (i), and a DC voltage within a range from 0.6 V to 3 V (for example, within a range from 1.2 V to 3 V) is applied between the second anode and the second cathode in process (ii). In this example, the first anode, the first cathode, the second anode and the second cathode may each be an electrode in which platinum exists at the electrode surface.

In one example of the present invention, the difference between the potential of the second anode and the potential of the second cathode may be gradually reduced in process (ii). By using this configuration, the concentration of free chlorine can sometimes be reduced in a shorter period of time, and the concentration of free chlorine can sometimes be reduced to an extremely low level. In those cases where the potential difference is reduced gradually, the potential difference may be reduced in a continuous manner, or the potential difference may be reduced in a stepwise manner. For example, the potential difference between the second anode and the second cathode may be set within a range from 2 V to 3 V in the initial stage of process (ii), and then the potential difference may be changed to a value of at least 1.2 V but less than 2 V. When the potential difference is reduced gradually, the final potential difference may be set within a range from 0.6 V to less than 1.2 V. For example, the potential difference between the second anode and the second cathode may be set within a range from 2 V to 3 V in the initial stage of process (ii), and then the potential difference may be changed to a value of at least 0.6 V but less than 1.2 V at the end of process (ii).

Unlike the method of Patent Document 1, in the method of the present invention, the concentration of free chlorine can be controlled without using an ion exchange material such as an ion exchange membrane. As a result, maintenance of the apparatus used for implementing the method of the present invention is simple. However, in the present invention, an ion exchange material may be used if necessary.

(Sterilization Method)

One example of the sterilization method of the present invention is described below. The sterilization method of the present invention is a method of performing sterilization using an aqueous solution containing free chlorine. This sterilization method includes the method of the present invention for controlling the concentration of free chlorine. In other words, this sterilization method includes processes (i) and (ii) described above in that order. Because the matters described above in relation to the method for controlling the concentration of free chlorine can also be applied to the sterilization method of the present invention, duplicate descriptions may sometimes be omitted. Further, the matters described in relation to the sterilization method of the present invention can also be applied to the method for controlling the concentration of free chlorine. Further, from another viewpoint, the term sterilization used in the present description can be replaced with the term washing. For example, the sterilization method and the sterilization apparatus of the present invention can be termed a washing method and a washing apparatus.

The sterilization method of the present invention includes a process of (I). In process (I), a sterilization target is sterilized using the aqueous solution (S) that has been treated in process (i). Because the aqueous solution (S) that has been treated in process (i) has an increased concentration of free chlorine, sterilization can be performed by process (I).

The sterilization method of the present invention may include, after process (I), process (II) washing the sterilization target using the aqueous solution (S) that has been treated in process (ii). The aqueous solution (S) that has been treated in process (ii) has a reduced concentration of free chlorine. Accordingly, executing process (II) can prevent a high concentration of free chlorine from being retained in the sterilization target. In those cases where process (II) is not performed, and the concentration of free chlorine is reduced using a washing water, a large amount of water requires to be used for the washing, but by performing process (II), the amount of such water used can be reduced.

There are no particular limitations on the target that is sterilized by the sterilization method of the present invention. Examples of the sterilization target include medical instruments, medical equipment, tableware, and other equipment and items. Examples of the medical instruments include blood treatment apparatus (for example, blood purification devices such as artificial dialysis devices). In particular, the tubing in a blood treatment apparatus (for example, the tubing through which the blood or the dialysis fluid flows) can be sterilized favorably. The sterilization method of the present invention is not limited to the medical field, and can also be used in other industrial fields.

In one example of the sterilization method of the present invention, the application of voltage in processes (i) and (ii) is conducted inside an electrolytic cell, and the sterilization target is sterilized by performing processes (i) and (ii) while the aqueous solution (S) is circulated between the electrolytic cell and the sterilization target. In other words, in this example, the sterilization is performed by the aqueous solution (S) that is circulated between the electrolytic cell and the sterilization target. By employing this configuration, satisfactory sterilization can be achieved with a minimal amount of the aqueous solution (S). Further, the amount of waste liquid when the aqueous solution (S) is discarded can be reduced. In one example of this configuration, the sterilization target is the tubing of a blood treatment apparatus.

The method of the present invention may also include, either between process (i) and process (ii), or after process (ii), maintaining the concentration of free chlorine in the aqueous solution (S) within a fixed range by adjusting the potentials of at least two electrodes selected from the plurality of electrodes. In the following description, this process may sometimes be termed "process (x)".

From another viewpoint, process (x) is adjusting the potential of a third anode and the potential of a third cathode in the aqueous solution (S), thereby maintaining the concentration of free chlorine in the aqueous solution (S) within a fixed range. The third anode and the third cathode are composed of one portion and one other portion of the plurality of electrodes, respectively.

When the aqueous solution (S) is constantly sterilized, or when the sterilization target for sterilization by the aqueous solution (S) is constantly sterilized, it is preferable that the concentration of free chlorine in the aqueous solution (S) is maintained within a fixed range. In such cases, process (x) can be performed favorably.

As illustrated in the Examples, by setting the potential difference between the anode and the cathode to a prescribed value or greater, the concentration of free chlorine increases, whereas by setting the potential difference to a prescribed value or less, the concentration of free chlorine decreases. Accordingly, by controlling the applied voltage, the concentration of free chlorine can be maintained within a fixed range. For example, when the concentration of free chlorine falls below the set range, a high voltage (for example, at least 4 V, and within a range from 4 V to 10 V in one particular example) may be applied, whereas when the concentration of free chlorine increases beyond the set range, a low voltage (for example, not more than 3 V, and within a range from 0.9 V to 3 V in one particular example) may be applied. Further, the concentration of free chlorine may also be maintained within a fixed range by continuous application of a prescribed voltage (for example, a voltage within a range from 1.8 V to 4.0 V).

The target values for the concentration of free chlorine in the aqueous solution (S) after the completion of process (i), after the completion of process (ii), and during process (x), may be set in accordance with the intended application. The concentration of free chlorine in the aqueous solution (S) after completion of process (i) may be within a range from 10 mg/L to 500 mg/L (for example, within a range from 100 mg/L to 300 mg/L). By employing this range, a superior sterilization effect can be obtained. Further, the concentration of free chlorine in the aqueous solution (S) after completion of process (ii) may be within a range from 0.01 mg/L to 10 mg/L (for example, within a range from 0.01 mg/L to 1 mg/L). By employing this range, the effects of residual free chlorine can be suppressed. Furthermore, the concentration of free chlorine during process (x) may be within a range from 1 mg/L to 100 mg/L (for example, within a range from 10 mg/L to 50 mg/L).

As described in Example 1, the pH can be increased by process (i). In other words, by treating a neutral aqueous solution (S) in process (i), an alkaline aqueous solution having a pH greater than 8 (for example, a weakly alkaline solution having a pH greater than 8 but not more than 10) and having a high concentration of free chlorine can be obtained. Alkaline aqueous solutions are effective in removing soiling such as oils, fats and proteins. Accordingly, the aqueous solution obtained by process (i) can be used favorably for the sterilized washing of a sterilization target having oils, fats, or proteins or the like adhered thereto. Specifically, the aqueous solution can be used favorably for sterilized washing or the like of the tubing of a blood treatment apparatus.

(Apparatus for Controlling Concentration of Free Chlorine)

One example of the apparatus of the present invention for controlling the concentration of free chlorine is described below. In this apparatus, processes (i) and (ii) are executed, and other processes (for example, process (x)) may also be executed as required. Because the matters described above in relation to the methods of the present invention can also be applied to the apparatus of the present invention, duplicate descriptions may sometimes be omitted. Further, the matters described in relation to the apparatus of the present invention can also be applied to the methods of the present invention.

The apparatus of the present invention includes a plurality of electrodes, a power source for applying a voltage to the plurality of electrode, and a controller for controlling the power source. The controller executes the aforementioned processes (i) and (ii) in that order.

The apparatus of the present invention may also include other equipment or members. For example, the apparatus may include a pump, valve, pipes for forming flow passages, a filter for filtering the aqueous solution (S), a tank for holding liquid, or any of various sensors or the like. Examples of tanks include a tank for holding the aqueous solution (S) to be treated in process (i), and tanks for holding the aqueous solution (S) that has been treated in each of the above processes. Examples of sensors include sensors for monitoring the concentration of free chlorine (dissolved chlorine, hypochlorous acid and hypochlorite ions), pH sensors, sensors for monitoring the amount and flow rate of the aqueous solution (S), and sensors for measuring the electrical conductivity of the aqueous solution (S). Conventionally known sensors may be used for these sensors. The sensors for monitoring the concentration of free chlorine include not only sensors that measure the concentration of free chlorine directly, but also sensors for measuring physical property values that indicate the concentration of free chlorine.

The apparatus of the present invention may include a device for adjusting the chloride ion concentration of the aqueous solution (S). For example, the apparatus of the present invention may include a device for preparing an aqueous salt solution (for example, an aqueous solution of sodium chloride) and adjusting the concentration of the aqueous salt solution.

The controller includes an arithmetic processing unit and a storage unit. The storage unit and the arithmetic processing unit may be integrated into a single device. Examples of the storage unit include storage memory and magnetic disks (such as hard disk drives). The programs used for executing the necessary processes (such as processes (i), (ii), (I), (II) and (x)) are stored in the storage unit. One example of the controller includes a large-scale integrated circuit (LSI). The controller is connected to a power source. The controller may also be connected to the types of equipment and sensors described above. The controller may execute each of the processes by controlling the various pieces of equipment (including the power source) based on the output from the sensors. The controller may also include an input device enabling a user to input commands, and/or a display device for displaying apparatus states.

The plurality of electrodes includes the anodes and cathodes described above. The plurality of electrodes may be composed of two electrodes. A DC power supply may be used as the power source. The power source may also be an AC-DC converter that converts the AC voltage obtained from an electrical outlet socket to a DC voltage. Alternatively, the power source may be a power generation device or battery (for example, a secondary battery) such as a solar cell or fuel cell.

The apparatus of the present invention usually includes a cell (electrolytic cell) in which the plurality of electrodes are disposed. The cell may be any vessel capable of storing the aqueous solution (S), and a cell made of resin is typically used.

(Sterilization Apparatus)

The sterilization apparatus of the present invention is a sterilization apparatus for performing sterilization using an aqueous solution containing free chlorine, and includes the apparatus of the present invention for controlling the concentration of free chlorine. The sterilization apparatus of the present invention may perform process (I), and may subsequently perform process (II). Further, the present invention can also be applied to an apparatus containing this sterilization apparatus. Examples of such apparatus include blood treatment apparatus (for example, blood purification devices such as artificial dialysis devices).

The sterilization apparatus that performs process (I) is an apparatus for sterilizing a sterilization target using an aqueous solution having a high concentration of free chlorine. By also performing process (II) in addition to process (I), the sterilization apparatus of the present invention can wash the sterilization target with an aqueous solution having a low concentration of free chlorine. As a result, the aqueous solution having a high concentration of free chlorine can be prevented from remaining on the sterilization target.

One example of the sterilization apparatus of the present invention may include an electrolytic cell in which the voltages of process (i) and process (ii) are applied (namely, an electrolytic cell having a plurality of electrodes). Processes (i) and (ii) (processes (I) and (II)) may then be performed in a state where the aqueous solution (S) is circulated between the electrolytic cell and the sterilization target. For example, a circulation flow passage may be formed between the electrolytic cell and the sterilization target, with the aqueous solution (S) then circulated through that flow passage. In process (I), the sterilization target is sterilized by the circulating aqueous solution (S). Further, in process (II), the sterilization target is washed by the circulating aqueous solution (S). By employing this configuration, the effects described above can be achieved.

As illustrated in the Examples, in the methods and apparatus of the present invention, the pH of the aqueous solution (S) can be adjusted by voltage application. Accordingly, the pH of the aqueous solution (S) may be controlled by voltage application. Further, the apparatus of the present invention may also include a mechanism for controlling the pH of the aqueous solution (S).

In the present invention, process (i) and process (ii) may be repeated, and process (I) and process (II) may be repeated.

In the above description, examples of embodiments were described in which processes (i) and (ii) are performed in that order. However, the following embodiments are also possible.

(A1) A method for controlling the concentration of free chlorine in which only process (i) is performed.

(A2) A method for controlling the concentration of free chlorine in which only process (ii) is performed.

(A3) A method for controlling the concentration of free chlorine in which process (i) and process (ii) are performed in any arbitrary order.

(A4) A sterilization method in which process (I) is performed without performing process (ii) (process (II)).

(A5) A washing method in which process (II) is performed without performing process (i) (process (I)).

(A6) A sterilization method in which process (I) and process (II) are performed in any arbitrary order.

(A7) A method for controlling the concentration of free chlorine or a sterilization method in which process (x) is also performed in any of the above methods of (A1) to (A6).

(A8) A method for controlling the concentration of free chlorine or a sterilization method in which only process (x) is performed.

(A9) An apparatus which executes any of the above methods of (A1) to (A8).

The methods of (A1) and (A4) can be used as methods for increasing the concentration of free chlorine in the aqueous solution (S), and as sterilization methods that use the aqueous solution (S). The methods of (A2) and (A5) can be used as methods for reducing the concentration of free chlorine in the aqueous solution (S), and as washing methods that use the aqueous solution (S). The method (A8) can be used as a method that maintains the concentration of free chlorine in the aqueous solution (S) at a constant level, and as a sterilization method that uses the aqueous solution (S).

When processes (i) and (ii) are performed, as described above, the potential difference between the electrodes in process (ii) is set to a smaller value than the potential difference between the electrodes in process (i). However, in the methods of (A2) and (A5), process (i) (process (I)) is not performed. Accordingly, the potential difference (voltage) between the second anode and the second cathode in process (ii) may be any potential difference that causes a decrease in the concentration of free chlorine. Further, in the methods of (A2) and (A5), the aqueous solution that is treated may or may not contain chloride ions. However, the aqueous solution that is treated is an aqueous solution that contains free chlorine.

Embodiments of the present invention are described below using a series of examples. In the embodiments described below, the case in which two platinum-coated electrodes are used is described as one specific example. However, the present invention is not limited to the embodiments described below.

Embodiment 1

In Embodiment 1, examples of the method and apparatus of the present invention are described. The apparatus of Embodiment 1 is illustrated in FIG. 1.

The apparatus 100 of FIG. 1 includes a cell 11, a power source 12, a controller 13, and an electrode pair 20. The electrode pair 20 is disposed inside the cell 11. In other words, the cell 11 is an electrolytic cell.

The electrode pair 20 includes a first electrode 21 and a second electrode 22. The power source 12 is connected to the first electrode 21 and the second electrode 22. Programs for executing each of the processes are stored in a storage unit of the controller 13. The controller 13 controls the voltage output from the power source 12 in accordance with those programs. An aqueous solution 30 that represents the aqueous solution (S) is stored in the cell 11.

Figure 2A:
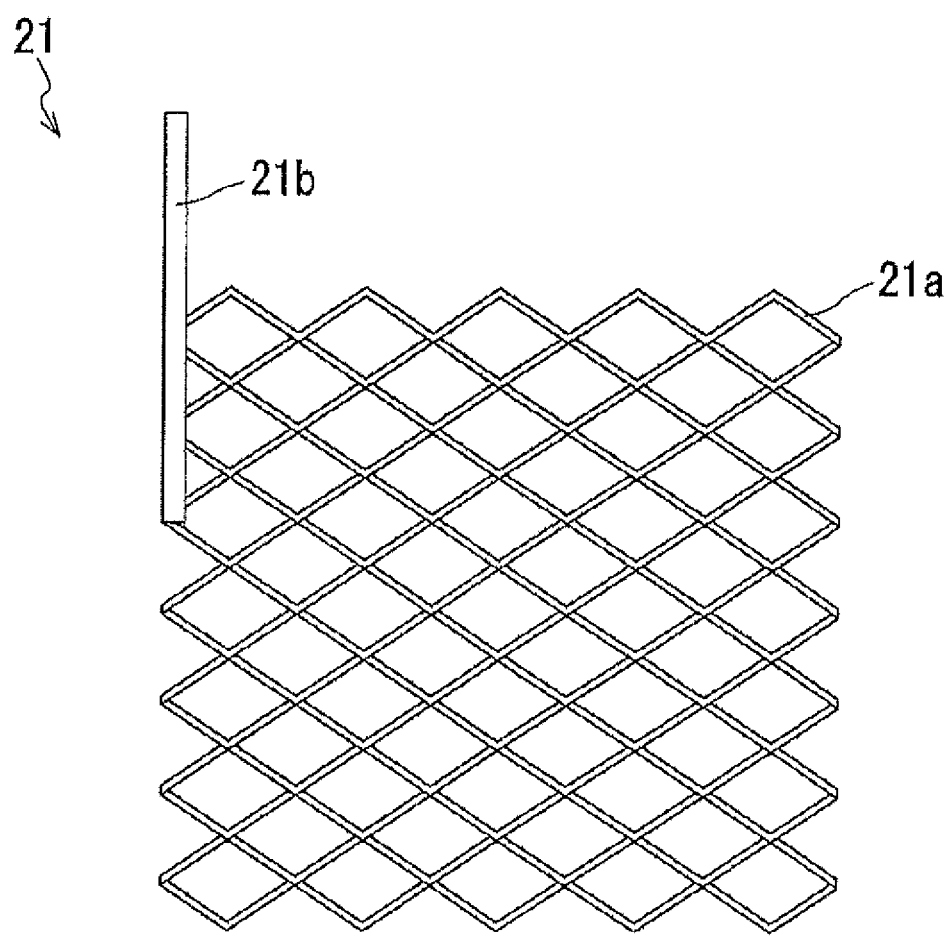
FIG. 2A is a front view schematically illustrating one example of an electrode used in the present invention.

A front view of one example of the first electrode 21 is illustrated in FIG. 2A. The first electrode 21 of FIG. 2A includes a net-like electrode 21a and a lead 21b connected thereto. The second electrode 22 also includes a similar net-like electrode and a lead. An expanded metal coated with platinum can be used as the net-like electrodes. The first electrode 21 may include a plurality of net-like electrodes, and the second electrode 22 may also include a plurality of net-like electrodes. By adjusting the number of net-like electrodes within each electrode, the ratio between the surface area of the first electrode 21 and the surface area of the second electrode 22 can be altered.

Figure 2B:
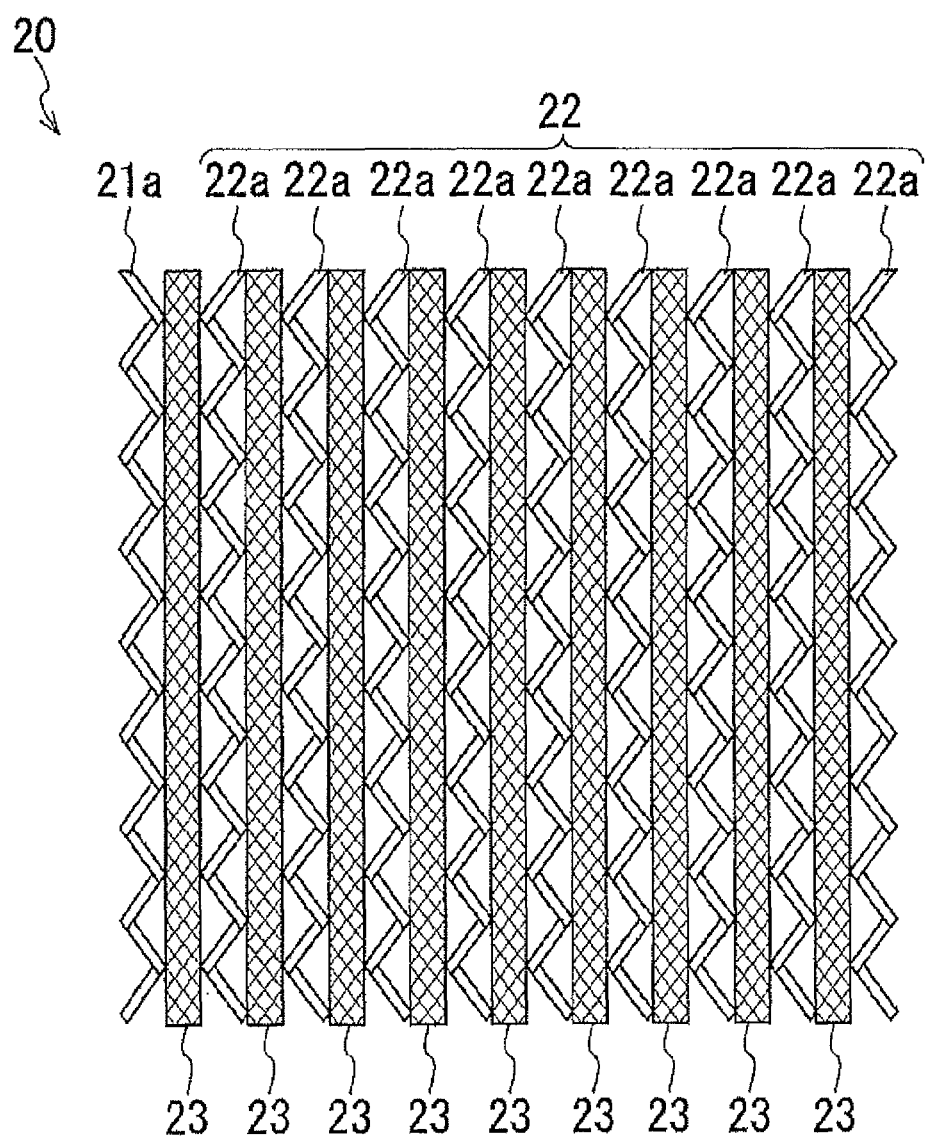
FIG. 2B is a diagram schematically illustrating one example of an electrode pair used in the present invention.

One example of the electrode pair 20 in the case where the second electrode 22 includes a plurality of net-like electrodes is illustrated schematically in FIG. 2B. FIG. 2B illustrates an example in which the first electrode 21 includes a single net-like electrode 21a, and the second electrode 22 includes 9 net-like electrodes 22a. Spacers 23 are disposed between the net-like electrodes, and the net-like electrodes and spacers 23 are stacked against each other. Leads are omitted in FIG. 2B, but the 9 net-like electrodes 22a are connected by leads. In the example in FIG. 2B, the net-like electrode 21a and the net-like electrodes 22a are not disposed alternately, but the two electrodes may also be disposed alternately.

One example of the operation of the apparatus 100 is described below. First, the controller 13 executes process (i). In process (i), a DC voltage is applied between the electrodes so that the first electrode 21 becomes the anode and the second electrode 22 becomes the cathode. The voltage at this time is a voltage that causes the concentration of free chlorine to increase, and is, for example, a voltage of at least 4 V (in one example a voltage within a range from 5 V to 12 V), or a voltage of at least 7 V (in one example a voltage within a range from 7 V to 9 V).

As a result of the voltage application, an oxygen gas production reaction caused by the electrolysis of water, and a production reaction for chlorine molecules due to chloride ion oxidation ($2Cl^- \rightarrow Cl_2 + 2e^-$) occur at the surface of the anode (the first electrode 21). A portion of the produced chlorine molecules become hypochlorous acid and hypochlorite ions. On the other hand, at the surface of the cathode (the second electrode 22), a hydrogen gas production reaction caused by the electrolysis of water, and a free chlorine decomposition reaction occur. The decomposition reaction of free chlorine includes a decomposition reaction of hypochlorous acid and a reduction reaction of chlorine molecules, as shown below.

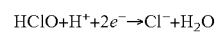

$$HClO + H^+ + 2e^- \rightarrow Cl^- + H_2O$$

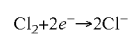

$$Cl_2 + 2e^- \rightarrow 2Cl^-$$

As described above, free chlorine is produced at the anode, whereas free chlorine is eliminated at the cathode. When the voltage is at least as high as a prescribed value (for example, at least 4 V), because the production rate of free chlorine exceeds the elimination rate of free chlorine, the concentration of free chlorine increases upon application of the voltage. The aqueous solution 30 treated by process (i) can be used for sterilization (for example, sterilized washing) as required.

Next, the controller 13 executes process (ii). In process (ii), a DC voltage is applied between the electrode 21 and electrode 22 so that one of the electrodes becomes the anode and the other becomes the cathode. For example, the voltage may be applied so that the first electrode 21 becomes the anode and the second electrode 22 becomes the cathode. Alternatively, the voltage may be applied so that the first electrode 21 becomes the cathode and the second electrode 22 becomes the anode. The voltage at this time is a voltage that causes the concentration of free chlorine to decrease, and is, for example, a voltage of not more than 3 V (in one example a voltage within a range from 0.9 V to 3.0 V), or a voltage of not more than 1.8 V (in one example a voltage within a range from 1.2 V to 1.8 V).

In a similar manner to the voltage application of process (i), upon the voltage application in process (ii), free chlorine is produced at the anode and free chlorine is eliminated at the cathode. However, in process (ii), by applying a lower voltage than that used in process (i), the elimination rate of free chlorine can be adjusted to exceed the production rate of free chlorine. As a result, in process (ii), the concentration of free chlorine decreases upon application of the voltage. The aqueous solution (S) for which the concentration of free chlorine has been reduced by process (ii) may be discarded, used for washing the sterilization target, or used for some other application.

Figure 3:
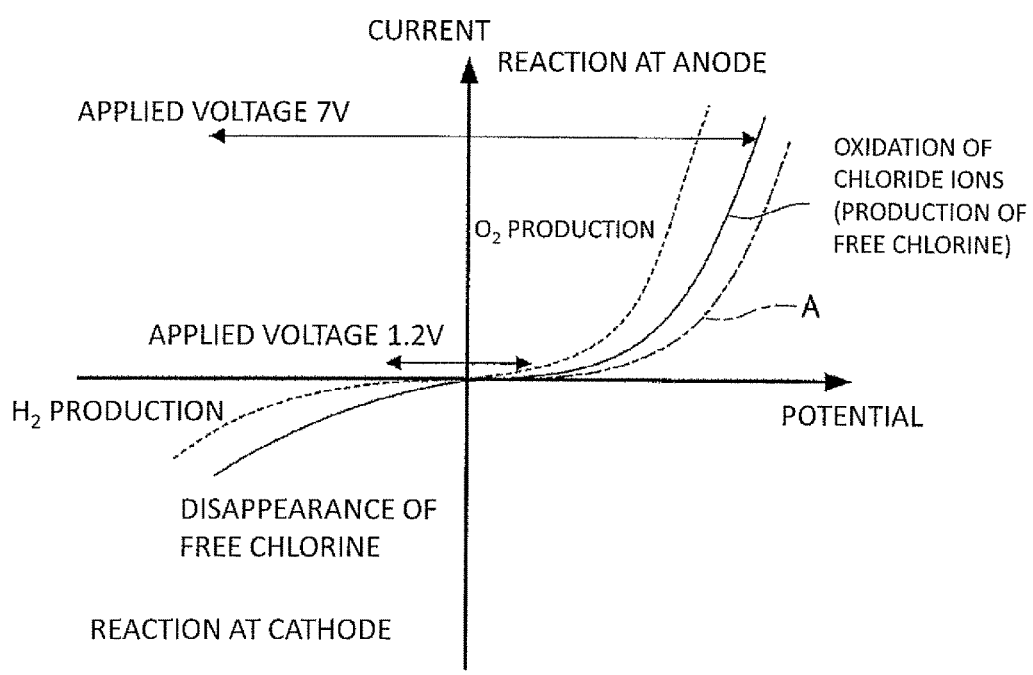
FIG. 3 is a conceptual drawing for describing the present invention.

The reason that the concentration of free chlorine is able to be controlled by the magnitude of the applied voltage is currently not completely clear. However, one possible reason is described using FIG. 3. The graph of FIG. 3 is a schematic graph predicted from test results, and may differ from actuality. Further, FIG. 3 is merely a schematic representation, and takes no consideration of the ratio between the magnitudes of the voltages.

The horizontal axis in FIG. 3 indicates the electrode potential, whereas the vertical axis in FIG. 3 indicates the reaction current. As illustrated in FIG. 3, in the reaction at the anode of Embodiment 1, the oxygen gas production reaction occurs more readily at a lower potential than the chloride ion oxidation reaction (free chlorine production reaction). Accordingly, by applying a low voltage, the oxygen gas production reaction can be initiated at the anode with almost no progression of the free chlorine production reaction. In other words, in process (ii), by adjusting the potential of the anode and the potential of the cathode (for example, by setting the DC voltage applied between the two electrodes to a suitable value), the elimination rate of free chlorine at the cathode can be increased to a higher rate than the production rate of free chlorine at the anode. As a result, the concentration of free chlorine can be reduced by process (ii).

In conventional methods for reducing the concentration of free chlorine by electrolysis, attention has been focused on enhancing the decomposition reaction of free chlorine at the cathode. For example, in Patent Document 2 mentioned above, no attention was paid to the reaction at the anode, and it was stated that applying the voltage so that no gas production occurred was preferable. In those cases where, as in the invention disclosed in Patent Document 2, the amount of free chlorine requiring decomposition is very small, the concentration of free chlorine can be reduced even at voltages where no gas production occurs. However, when the amount of free chlorine requiring decomposition is large, an adequate current requires to be passed between the electrodes by causing a reaction accompanied by gas generation at the anode. The inventors of the present invention discovered that in order to efficiently reduce the amount of free chlorine, it was necessary to focus attention not only on the free chlorine decomposition at the cathode, but also on the electrolysis at the anode.

In order to efficiently reduce the concentration of free chlorine, it is necessary to suppress the chloride ion oxidation reaction (namely, the free chlorine production reaction) at the anode. Accordingly, for the reaction at the anode in FIG. 3, it is preferable to shift the curve for the chloride ion oxidation reaction toward the right, and/or to reduce the angle between the curve for the chloride ion oxidation reaction and the horizontal axis. The inventors of the present invention were the first to focus their attention on these matters, and discovered that by employing the conditions described below, the curve for the chloride ion oxidation reaction could be altered in the manner described above. Specifically, those conditions are the conditions (J1) to (J3) described below.

(J1) The anode in process (ii) is an electrode in which platinum exists at the surface (a platinum-coated electrode). Platinum exhibits a large difference between the overvoltage for the oxygen gas production reaction and the overvoltage for the chloride ion oxidation reaction, and therefore by using a platinum-coated electrode, the chloride ion oxidation reaction can be suppressed.

(J2) An aqueous solution (S) having a chloride ion concentration not higher than a prescribed value is used. By using an aqueous solution (S) having a low chloride ion concentration, the chloride ion oxidation reaction can be suppressed. Specifically, an aqueous solution having a chloride ion concentration of not more than 582 mmol/L may be used, and for example, an aqueous solution having a chloride ion concentration within a range from 17 mmol/L to 582 mmol/L (or within a range from 86 mmol/L to 205 mmol/L in one example) may be used. In those cases where the aqueous solution (S) is an aqueous solution of sodium chloride, the concentration may be within a range from 0.1 wt % to 3.4 wt % (or within a range from 0.5 wt % to 1.2 wt % in one example).

(J3) The hydrogen ion concentration in the vicinity of the anode is lowered. When electrolysis of water occurs, the hydrogen ion concentration in the vicinity of the anode increases. When the hydrogen ion concentration in the vicinity of the anode increases, the solution becomes acidic, facilitating the production of hypochlorous acid. Accordingly, in process (ii), it is preferable that the hydrogen ion concentration in the vicinity of the anode is lowered. Examples of methods for lowering the hydrogen ion concentration in the vicinity of the anode include the methods described below.

(J3-1) The flow rate of the aqueous solution (S) in the vicinity of the anode is increased, thereby promoting the diffusion of hydrogen ions in the vicinity of the anode. For example, the average flow rate of the aqueous solution (S) flowing through the inside the electrolytic cell may be set to a value of at least 3.5 mm/s, or at least 6 mm/s. Although there are no particular limitations on the upper limit for the average flow rate, a value of not more than 30 mm/s may be used.

(J3-2) The anode is moved, thereby agitating the aqueous solution (S) in the vicinity of the anode and promoting the diffusion of hydrogen ions in the vicinity of the anode. For example, by rotating the anode, the aqueous solution (S) in the vicinity of the anode can be agitated.

(J3-3) A structure that causes turbulence flow in the vicinity of the anode is used, thereby agitating the aqueous solution (S) in the vicinity of the anode and promoting the diffusion of hydrogen ions in the vicinity of the anode. For example, turbulence may be generated by providing unevenness on the surface of the anode. Further, turbulence may also be generated in the vicinity of the anode by the spacers disposed between the electrodes.

By satisfying the above conditions, the curve for the chloride ion oxidation reaction can be moved as illustrated by the alternate long and short dash line A in FIG. 3. As a result, the concentration of free chlorine can be efficiently reduced in process (ii). An effect can be achieved by implementing any one of the above conditions (J1) to (J3), but the effect can be enhanced by combining a plurality of the conditions. Specifically, combinations of (J1) and (J2), (J1) and (J3), (J2) and (J3), or (J1), (J2) and (J3) may be satisfied. Further, in addition to these conditions, condition (J4) described below may also be satisfied.

On the other hand, by applying a high voltage, the production rate of free chlorine at the anode can be increased so as to exceed the elimination rate of free chlorine at the cathode. As a result, the voltage application in process (i) enables the concentration of free chlorine to be increased.

In one example, process (i) and process (ii) may be performed such that condition (J4) described below is satisfied.

(J4) In process (i), a DC voltage of at least 4 V (for example, within a range from 4 V to 12 V) is applied between the first anode and the first cathode, and in process (ii), a DC voltage within a range from 0.6 V to 3 V is applied between the second anode and the second cathode. For example, a DC voltage of at least 5 V (for example, within a range from 5 V to 8 V) is applied in process (i), and a DC voltage within a range from 0.9 V to 3 V (for example, within a range from 1.2 V to 3 V) is applied in process (ii).

Further, in process (i) and process (ii), the potential difference between the electrodes (the applied voltage) may be altered as the treatment progresses. For example, in the initial stage of process (ii), a DC voltage within a range from 1.8 to 3.0 V may be applied between the electrodes, and then when the concentration of free chlorine decreases to 50 mg/L, a DC voltage of at least 1.2 V but less than 1.8 V may be applied. By applying voltage in this manner, the rate of reduction in the concentration of free chlorine may sometimes be able to be increased.

In the present invention, at least one condition selected from the group consisting of (J1), (J2), (J3) and (J4) may be satisfied. For example, processes (i) and (ii) may be performed in such a manner that all of (J1) to (J4) are satisfied.

From another viewpoint, process (ii) maybe replaced with a process (ii'). In process (ii'), the concentration of free chlorine in the aqueous solution (S) is reduced by applying a DC voltage between two electrodes selected from the plurality of electrodes, in a state where at least one condition selected from the group consisting of (J1), (J2), (J3) and (J4) is satisfied.

In one example of the present invention, the anode and the cathode in process (i), and the anode and the cathode in process (ii) may all be electrodes in which platinum exists at the electrode surface, and the above condition (J4) may be satisfied. In this case, an aqueous solution (S) having a chloride ion concentration within a range from 17 mmol/L to 582 mmol/L (or within a range from 86 mmol/L to 205 mmol/L in one example) may be used. Moreover, the average flow rate of the aqueous solution (S) flowing around the periphery of the anode and the cathode in process (ii) may be at least 3.5 mm/s. The average flow rate of the aqueous solution (S) inside the cell in which the anode and the cathode are disposed can be considered as the average flow rate of the aqueous solution (S) flowing around the periphery of the anode and the cathode.

One method of increasing the average flow rate of the aqueous solution (S) flowing through the electrolytic cell involves reducing the cross-sectional area (C) of the electrodes, the cross-sectional area (C) being perpendicular to the direction of flow of the aqueous solution (S). If the amount of the aqueous solution (S) flowing through the electrolytic cell per unit of time is the same, then the smaller the cross-sectional area (C) becomes, the faster the average flow rate of the aqueous solution (S) flowing through the electrolytic cell will become. In order to reduce the cross-sectional area (C) without reducing the electrode surface area, the electrolytic cell and the electrodes disposed therein may be formed as elongated rectangular shapes, with the aqueous solution (S) then set to flow along the lengthwise direction.

Figure 5:
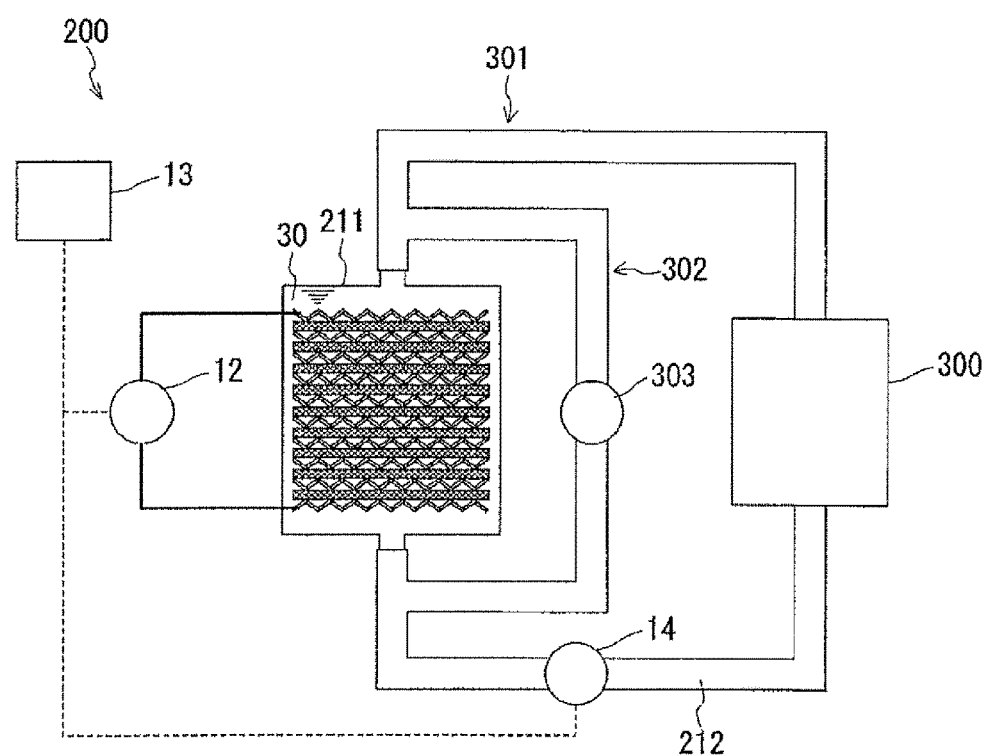
FIG. 5 is a schematic view illustrating yet another example of an apparatus of the present invention.

Further, the average flow rate of the aqueous solution (S) flowing through the electrolytic cell (or from another viewpoint, the average flow rate of the aqueous solution (S) flowing in the vicinity of the electrodes) may be set to different values in process (i) and process (ii). Specifically, the aforementioned average flow rate in process (i) may be slower than the average flow rate in process (ii). By slowing the average flow rate in process (i), the electric double layer at the electrode surface can be maintained, and the concentration of free chlorine can be increased efficiently. On the other hand, by increasing the average flow rate in process (ii), as described above, the concentration of free chlorine can be efficiently reduced in process (ii). Examples of the method for altering the average flow rate between process (i) and process (ii) include the following three methods. In a first method, the pump and valves are simply adjusted to alter the amount of the aqueous solution (S) flowing through the electrolytic cell per unit of time. This configuration illustrated below in FIG. 5 is included in this first method. In the second method, a rectangular electrolytic cell (and a rectangular electrode group disposed inside the cell) are used, and the direction in which the aqueous solution (S) flows is altered between process (i) and process (ii). Specifically, the aqueous solution (S) is set to flow in a direction perpendicular to the direction in which the cross-sectional area of the electrolytic cell is larger in process (i), and set to flow in a direction perpendicular to the direction in which the cross-sectional area of the electrolytic cell is smaller in process (ii). In the third method, the electrolytic cell is altered between process (i) and process (ii). In this case, a plurality of electrolytic cells having different cross-sectional areas are used.

Embodiment 2

In Embodiment 2, examples of the method and apparatus for circulating the aqueous solution (S) between an electrolytic cell and a region outside the electrolytic cell are described. An apparatus 200 of Embodiment 2 is illustrated in FIG. 4.

Referring to FIG. 4, the apparatus 200 includes a cell 211, a power source 12, a controller 13, a pump 14, and an electrode pair 20. The electrode pair 20 is disposed inside the cell 211. In other words, the cell 211 is an electrolytic cell. The power source 12, the controller 13 and the electrode pair 20 were described above in Embodiment 1, and duplicate descriptions of these items are omitted. FIG. 4 illustrates an example in which the electrode pair 20 illustrated in FIG. 2B is used.

An inlet 211a and an outlet 211b are formed in the cell 211. A passage 212 is connected between the inlet 211a and the outlet 211b so as to form a circulation passage 301 including a sterilization target 300. The aqueous solution 30 that represents the aqueous solution (S) is circulated through the circulation passage 301 by the pump 14 under the control of the controller 13. If necessary, a passage or tank for supplying the aqueous solution 30, and a passage or tank for discharging the aqueous solution 30 following its use in the sterilization may also be connected to the circulation passage 301.

There are no particular limitations on the positions in which the inlet 211a and the outlet 211b are formed, and as illustrated in FIG. 4, the inlet 211a may be formed at the bottom of the cell 211 and the outlet 211b formed at the top of the cell 211. By employing this configuration, gas that is produced at the surfaces of the electrodes can be removed rapidly from the electrode surfaces. As a result, any deterioration in the rate of the electrolysis reaction due to gas on the surfaces of the electrodes can be suppressed.

As illustrated in FIG. 4, the net-like electrodes may be disposed so that the in-plane direction of the net-like electrodes is orthogonal to the flow of the aqueous solution 30. Further, the first electrode 21 having a small surface area may be disposed on the side of the inlet 211a, and process (ii) may be performed with a voltage applied such that the first electrode 21 becomes the anode. By using these configurations, the concentration of free chlorine can be reduced efficiently.

In the apparatus 200, process (I) (the sterilization process including process (i)) is performed in a state where the aqueous solution 30 is circulated between the cell 211 and the sterilization target 300. Moreover, in the apparatus 200, process (II) (the washing process including process (ii)) may also be performed in a state where the aqueous solution 30 is circulated between the cell 211 and the sterilization target 300. Process (i) and process (ii) can be executed using the same method as that described for Embodiment 1.

One example of the sterilization target 300 is tubing. By using the apparatus 200, sterilized washing of the inside of the tubing can be achieved. Examples of the tubing include the tubing of a blood treatment apparatus. The tubing through which the dialysis fluid passes requires sterilization after use. On the other hand, when sterilization is performed using free chlorine, the concentration of residual free chlorine in the tubing requires to be reduced before dialysis can be restarted. By using the present invention, the inside of the tubing can be subjected to sterilized washing by process (I), and the concentration of free chlorine inside the tubing can then be reduced by process (II). Accordingly, the present invention can be used favorably for sterilization of the tubing inside a blood treatment apparatus. The sterilization may be performed by providing a sterilization tank at the position of the sterilization target 300, and then immersing the articles that are to be subjected to sterilized washing in the aqueous solution (S) inside that sterilization tank. Further, the cell 11 of Embodiment 1 may be used as the sterilization tank.

The voltage application times during process (i) and process (ii) may be set in accordance with the desired purpose. A sensor for monitoring the concentration of free chlorine may be placed inside the cell or inside the flow passage. The controller may control the magnitude of the voltage and the time of the voltage application based on the output from the sensor. Further, the controller may also apply the voltage in accordance with predetermined conditions.

As illustrated in FIG. 5, the apparatus may be constructed so that the cell 211 forms a part of two circulation passages. In the configuration shown in FIG. 5, a circulation passage 302 is formed in parallel with the circulation passage 301. The flow volume of the aqueous solution (S) through the circulation passage 302 is controlled by a pump 303 provided within the circulation passage 302. By increasing the flow rate of the aqueous solution (S) through the circulation passage 302, the flow rate (average flow rate) of the aqueous solution (S) inside the cell 211 can be increased independently of the flow rate of the aqueous solution (S) through the circulation passage 301.

Examples of apparatus for executing processes (i) and (ii) have been described above in Embodiments 1 and 2. However, these apparatus can also execute any of the methods (A1) to (A8) described above.

EXAMPLES

The present invention is described below in further detail using a series of examples. In the examples, the concentration of free chlorine was measured using the method described below.

(Method for Measuring Concentration of Free Chlorine)

The concentration of free chlorine was measured by the DPD method (diethyl-para-phenylenediamine method). Specifically, measurement was performed by a free chlorine measurement method (Method 8021 described by Hach Company) using an absorption photometer (DR3900) manufactured by Hach Company. In this method, the sample and a reagent for measuring the concentration of free chlorine are placed in a sample cell, and the concentration of free chlorine is calculated by measuring the absorbance of the sample which has developed color due to the reagent.

Example 1

In Example 1, the relationship between the applied voltage in process (i) and the concentration of free chlorine was investigated.

In Example 1, an electrode pair having the configuration illustrated in FIG. 2B was used. Electrodes (length: 35 mm, width: 54 mm, thickness: 1.8 mm) formed from titanium expanded metal that had been plated with platinum were used for the net-like electrodes that formed the anode and the cathode. As illustrated in FIG. 2B, the first electrode 21 (the anode in this example) was prepared using a single net-like electrode 21a, whereas the second electrode 22 (the cathode in this example) was prepared using 9 net-like electrodes 22a. With the electrodes in Example 1, the surface area of the cathode was about 9 times the surface area of the anode. Net-like resin spacers (thickness: 0.8 mm) were disposed between each of the electrodes.

First, an aqueous solution of sodium chloride (physiological saline solution) with a concentration of 0.9 wt % was prepared. This aqueous solution was subjected to process (i). Specifically, the electrodes described above were placed in a beaker containing the aqueous solution, and a DC voltage was applied between the first electrode 21 (anode) and the second electrode 22 (cathode). The voltage application was performed while the aqueous solution was stirred with a stirrer. Further, the aqueous solution inside the beaker was circulated at a flow rate of 150 mL/minute using a pump. The total volume of the aqueous solution was 1 L. In Example 1, four types of tests were performed using different voltage application methods. Specifically, the voltage was applied under the four sets of conditions described below.

(Test 1-1) Application of 5 V constant voltage
(Test 1-2) Application of 7 V constant voltage
(Test 1-3) Application of 10 V constant voltage
(Test 1-4) Voltage applied so that a constant current of 2 A flowed between the electrodes (the applied voltage was about 8.5 V)

Figure 6:
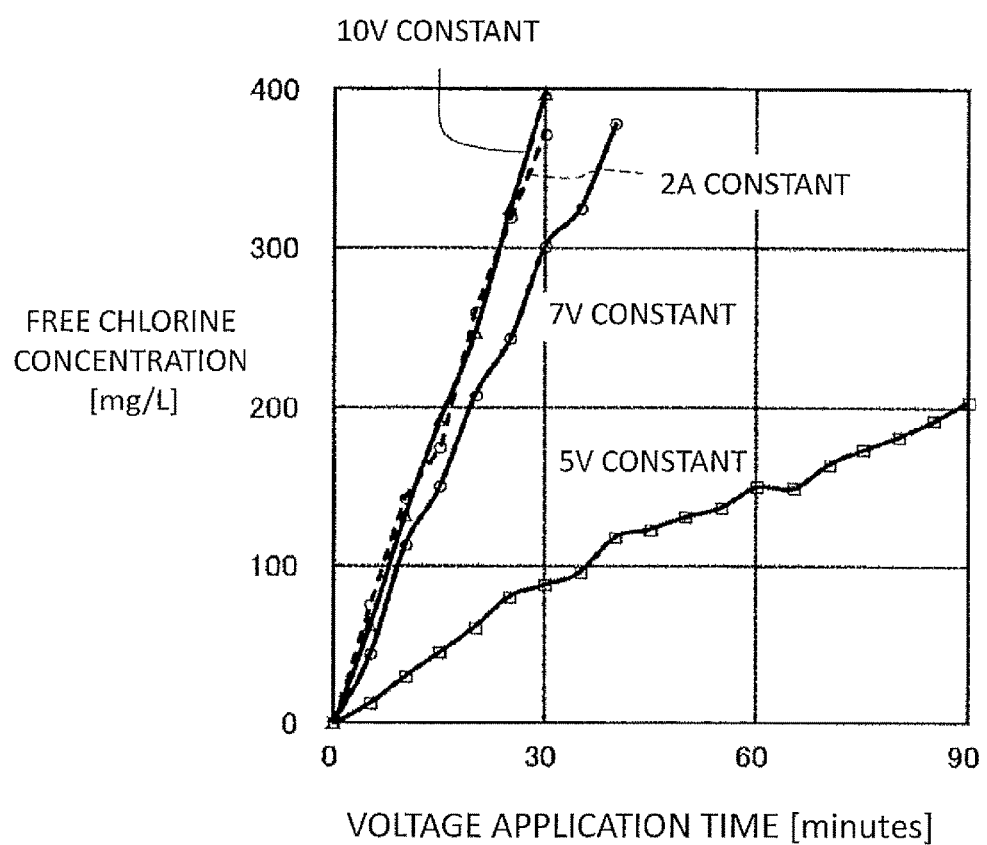
FIG. 6 is a graph illustrating test results from Example 1.

In each of the above tests, the relationship between the voltage application time and the concentration of free chlorine was investigated. The results are illustrated in FIG. 6. As illustrated in FIG. 6, by applying a voltage of at least 5 V, the concentration of free chlorine was able to be increased. The higher the voltage, the greater the rate of increase in the concentration of free chlorine.

Figure 7:
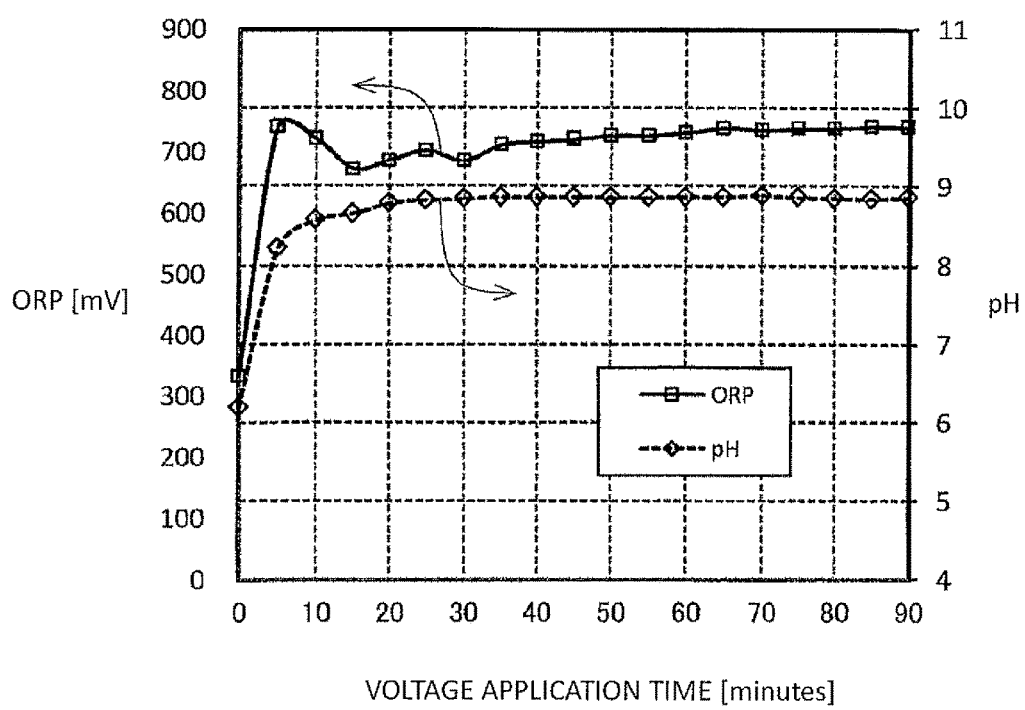
FIG. 7 is a graph illustrating other test results from Example 1.

Further, the changes in the ORP (oxidation reduction potential) and the pH of the aqueous solution when a voltage of 5 V was applied are illustrated in FIG. 7. As illustrated in FIG. 7, when a voltage of 5 V was applied, the ORP and the pH increased in the initial stages of voltage application, but were then substantially constant thereafter.

Example 2

In Example 2, the relationship between the applied voltage in process (ii) and the concentration of free chlorine was investigated. In Example 2, with the exception of altering the applied voltage, tests were performed under the same conditions as Example 1.

In Example 2, a voltage was first applied for 15 minutes so that a constant current of 2 A flowed between the first electrode 21 (anode) and the second electrode 22 (cathode) described in Example 1 (process (i)). The voltage application in process (i) caused the concentration of free chlorine in the aqueous solution (physiological saline solution) to reach about 200 mg/L (specifically, within a range from 181 to 251 mg/L).

Figure 8A:
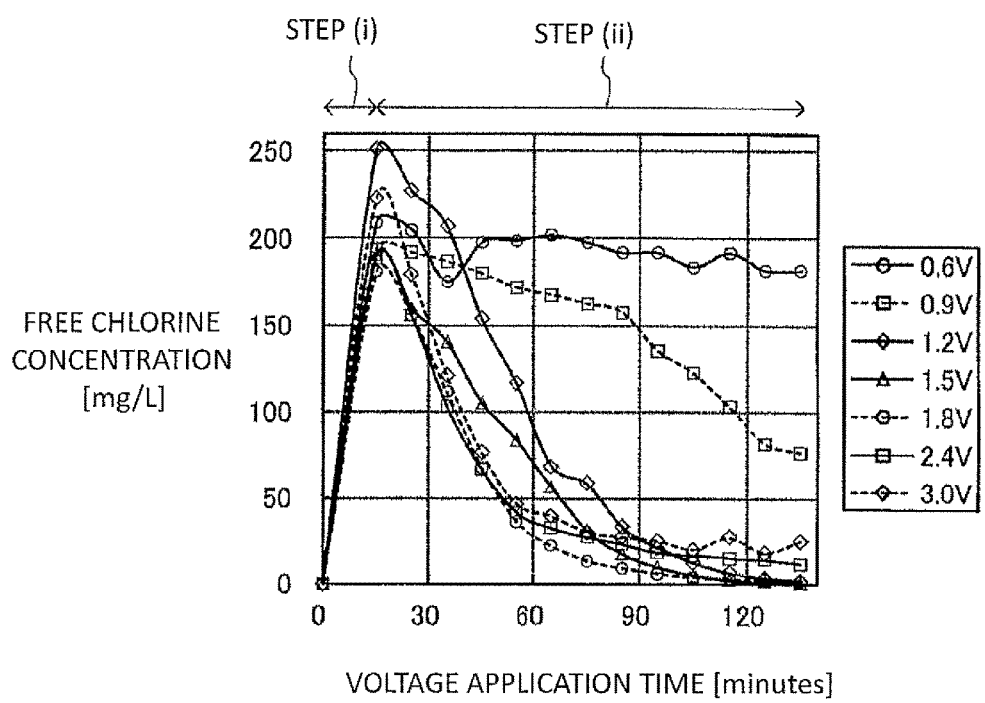
FIG. 8A is a graph illustrating test results from Example 2.
Figure 8B:
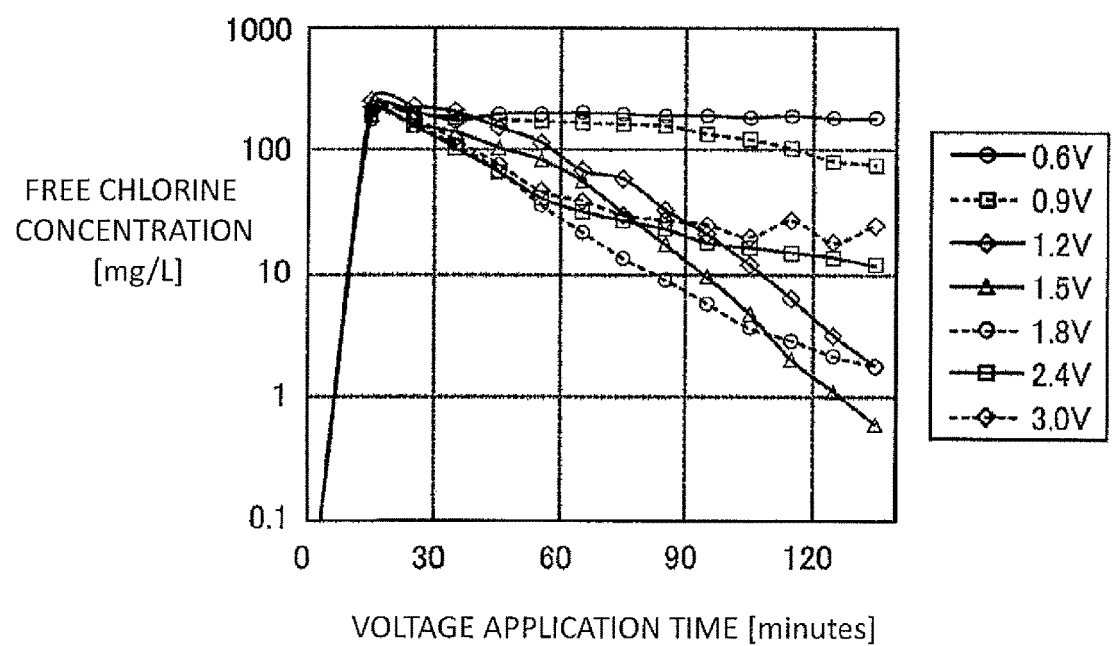
FIG. 8B is another graph illustrating test results from Example 2.

Next, the process (ii) was performed. In Example 2, 7 tests were performed with different applied voltages. Specifically, tests were performed in which the fixed voltage applied between the first electrode 21 (anode) and the second electrode 22 (cathode) was set to 0.6 V (Test 2-1), 0.9 V (Test 2-2), 1.2 V (Test 2-3), 1.5 V (Test 2-4), 1.8 V (Test 2-5), 2.4 V (Test 2-6) and 3.0 V (Test 2-7). Then, the relationship between the concentration of free chlorine in the aqueous solution and the voltage application time was investigated. The measurement results are illustrated in FIG. 8A. Further, a graph in which the vertical axis of FIG. 8A has been displayed as a logarithmic scale is illustrated in FIG. 8B. In FIG. 8A and FIG. 8B, the voltage application time from 0 to 15 minutes corresponds with process (i), and the subsequent time period corresponds with process (ii). The voltages shown in the legends of FIG. 8A and FIG. 8B represent the voltages applied in process (ii).

As illustrated in FIG. 8A and FIG. 8B, the concentration of free chlorine decreased as a result of performing process (ii). The concentration of free chlorine decreased greatly when the applied voltage was within a range from 0.9 to 3.0 V, and decreased even more when the applied voltage was within a range from 1.2 to 3.0 V (and particularly within a range from 1.2 V to 1.8 V). When the salt concentration in the aqueous solution was high, setting the applied voltage within a range from 1.8 V to 3.0 V enabled the rate of reduction in the concentration of free chlorine to be increased.

As illustrated in FIG. 8A and FIG. 8B, in the initial stages of process (ii), the rate of reduction in the concentration of free chlorine was large when the applied voltage was within a range from 2.4 V to 3.0 V. However, as the voltage application was continued, the concentration of free chlorine became lower in those tests where the applied voltage was within a range from 1.2 to 1.8 V. These results suggest that it may be possible to apply a voltage within a comparatively high voltage range (for example, 2.4 V to 3.0 V) in the initial stages of process (ii), and subsequently apply a lower voltage (for example, 1.2 V to 1.8 V). By using such a configuration, the concentration of free chlorine can be reduced in a shorter period of time.

Figure 9:
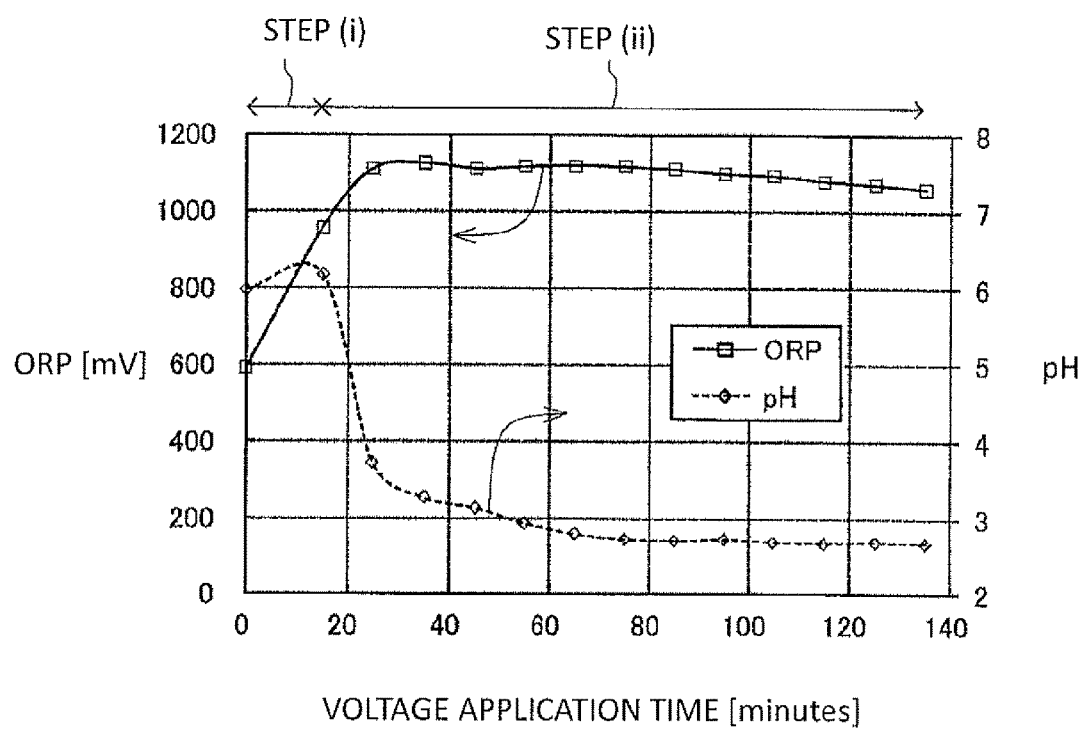
FIG. 9 is a graph illustrating other test results from Example 2.

The changes in the ORP and the pH of the aqueous solution in Test 2-5 (an applied voltage of 1.8 V in process (ii)) are illustrated in FIG. 9. As illustrated in FIG. 9, when a voltage of 1.8 V was applied, the ORP increased and the pH decreased in the period when the voltage application time shown in FIG. 9 was between 15 minutes (the start of process (ii)) and 30 minutes, but after that period, there was no significant change in either property.

As shown in Examples 1 and 2, regardless of the fact that the same electrodes were used in process (i) and process (ii), the concentration of free chlorine was able to be increased and reduced by altering the applied voltage. The fact that the chlorine concentration could be controlled using this type of method was completely unknown until now. The present invention is based on this novel discovery from the research of the inventors of the present invention that the type of control described above was possible.

Example 3

In Example 3, tests were performed in which the ratio between the surface area of the anode and the surface area of the cathode was altered. For the cathode, the second electrode 22 described in Example 1, namely an electrode containing 9 net-like electrodes 22a, was used. For the net-like electrode of the anode, the net-like electrode 21a described in Example 1 was used, but the number of these net-like electrodes constituting the anode was varied from one to nine. The configurations of the electrodes used in Example 3 are shown in Table 1. As shown in Table 1, the value of (surface area of cathode)/(surface area of anode) was altered within a range from 1.0 (Test 3-5) to 9.0 (Test 3-1). The tests were performed using a batch system such as that illustrated in FIG. 1, and a voltage was applied between the electrodes while the solution was stirred with a stirrer.

TABLE 1

|  | Number of net-like electrodes | | Surface area ratio |
|---|---|---|---|
|  | Cathode | Anode | cathode/anode |
| Test 3-1 | 9 | 1 | 9.0 |
| Test 3-2 | 9 | 2 | 4.5 |
| Test 3-3 | 9 | 3 | 3.0 |
| Test 3-4 | 9 | 6 | 1.5 |
| Test 3-5 | 9 | 9 | 1.0 |

In Example 3, with the exception of changing the configuration of the electrode pair, tests were performed under the same conditions as Test (2-3) of Example 2. Specifically, a voltage was first applied for 15 minutes so that a constant current of 2 A flowed between the anode (the first electrode 21) and the cathode (the second electrode 22) (process (i)). The voltage application in process (i) caused the concentration of free chlorine to reach about 200 mg/L (specifically, within a range from 194 to 251 mg/L).

Figure 10:
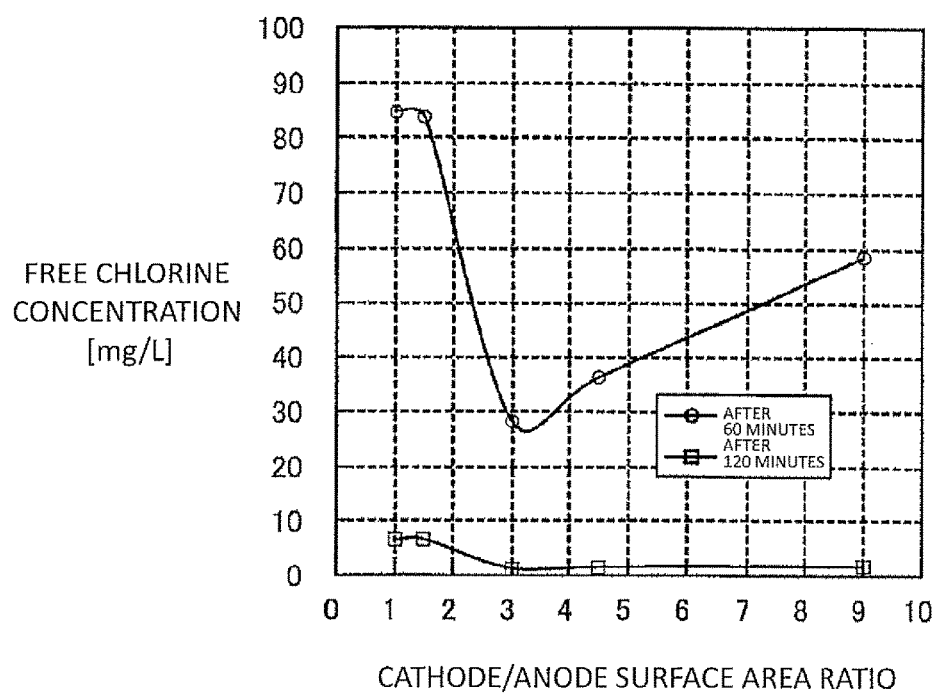
FIG. 10 is a graph illustrating test results from Example 3.

Subsequently, process (ii) of any of Tests 3-1 to 3-5 was performed. Specifically, a constant voltage of 1.2 V was applied between the anode (the first electrode 21) and the cathode (the second electrode 22). Then, the change in the concentration of free chlorine in the aqueous solution as a result of process (ii) was measured. The measurement results are illustrated in FIG. 10. As illustrated in FIG. 10, at a point 60 minutes after the start of the voltage application of process (ii), the concentration of free chlorine had decreased greatly in those cases where the cathode/anode surface area ratio was within a range from 3.0 to 9.0. On the other hand, at a point 120 minutes after the start of the voltage application of process (ii), the difference in effect due to the cathode/anode surface area was small. The rate of reduction in the concentration of free chlorine was greater in Tests 3-2 and 3-3 when the cathode/anode surface area ratio was within a range from 3.0 to 4.5, than in Test 3-1 when the surface area ratio was 9.0, but the reason for this effect is unclear. Because these results represent the results of tests performed using a batch system, there is a possibility that a relative lack of movement in the aqueous solution in the vicinity of the electrodes may have had an effect. If the movement of the aqueous solution in the vicinity of the electrodes is minimal, then the acid concentration in the vicinity of electrodes may increase, facilitating the production of hypochlorous acid.

The results in FIG. 10 indicate that by setting the cathode/anode surface area ratio within a range from 3.0 to 9.0, the rate of reduction in the concentration of free chlorine can be increased. Further, the results in FIG. 10 also indicate that in those cases where the voltage is applied for a long period of time, the concentration of free chlorine can be reduced satisfactorily even when the cathode/anode surface area ratio is large (namely, even if the area of anode used is small).

Example 4

In Example 4, the relationship between the concentration of the alkali metal chloride in the aqueous solution and the change in the concentration of free chlorine was investigated. Specifically, processes (i) and (ii) were performed using different concentrations of the alkali metal chloride in the aqueous solution. The electrode pair used had the same configuration as the electrode pair of Example 1.

First, a plurality of aqueous solutions having different concentrations of sodium chloride were prepared. Specifically, a plurality of aqueous solution of sodium chloride having concentrations within a range from 0.7 wt % to 10.8 wt % were prepared. Process (i) was performed using each of these aqueous solution of sodium chloride. Specifically, the electrode pair described above was placed in a beaker containing 200 mL of the aqueous solution, and a voltage was applied for 3 minutes so that a constant current of 2 A flowed between the first electrode 21 (anode) and the second electrode 22 (cathode). The voltage application was performed while the aqueous solution was stirred with a stirrer. As a result of this voltage application, the concentration of free chlorine in the aqueous solution reached about 200 mg/L.

Figure 11:
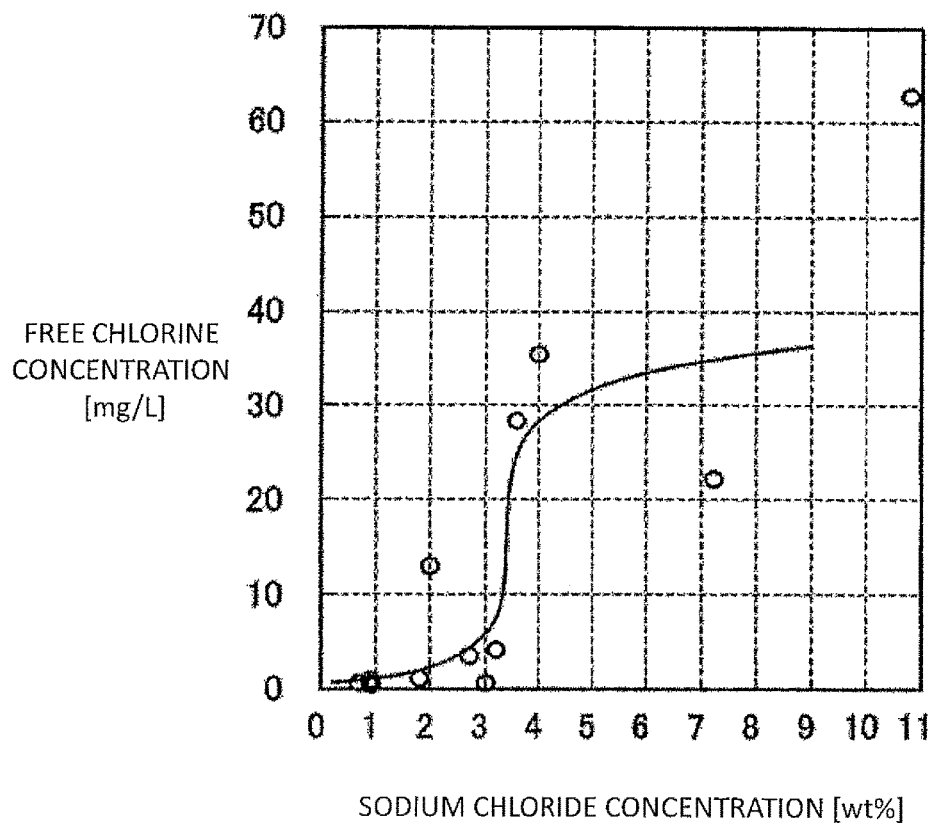
FIG. 11 is a graph illustrating test results from Example 4.

Subsequently, process (ii) was performed. In process (ii), a constant voltage of 1.2 V was applied between the first electrode 21 (anode) and the second electrode 22 (cathode). Then, the change in the concentration of free chlorine due to process (ii) was measured. The concentration of free chlorine after process (ii) is illustrated in FIG. 11. The sodium chloride concentration and the length of time of the voltage application in process (ii) were as shown in Table 2.

TABLE 2

| | Sodium chloride concentration (wt %) | Voltage application time (minutes) |
| --- | --- | --- |
| Test 4-1 | 0.7 | 40 |
| Test 4-2 | 0.9 | 30 |
| Test 4-3 | 0.9 | 40 |
| Test 4-4 | 1.8 | 50 |
| Test 4-5 | 2.0 | 60 |
| Test 4-6 | 2.7 | |
| Test 4-7 | 3.0 | |
| Test 4-8 | 3.2 | |
| Test 4-9 | 3.6 | |
| Test 4-10 | 4.0 | |
| Test 4-11 | 7.2 | |
| Test 4-12 | 10.8 | |

As illustrated in FIG. 11, when the concentration of sodium chloride was within a low range, the reduction in the concentration of free chlorine was large. When the concentration of sodium chloride was within a range from 0.7 to 3.2 wt % (and particularly within a range from 0.7 to 3.0 wt %), the concentration of free chlorine decreased greatly. It may be considered that 1 L of a 1 wt % aqueous solution of sodium chloride contains approximately (10/58.4)=0.171 mol (171 mmol) of chloride ions. If the chloride ion concentration is considered on this basis, then the concentration of free chlorine decreased greatly when the chloride ion concentration was within a range from 120 mmol/L to 548 mmol/L (and particularly within a range from 120 mmol/L to 514 mmol/L).

Example 5

In Example 5, the anode was changed, and the same tests as Example 4 were performed. In Example 5, the concentration of the aqueous solution of sodium chloride was varied within a range from 0.9 wt % to 3.6 wt % (specifically, 0.9 wt %, 1.35 wt %, 1.8 wt % and 3.6 wt %), and the voltage application was performed for 60 minutes in process (ii). With the exception of these changes, tests were performed under the same conditions as those described for Example 4.

In Example 5, an electrode in which iridium oxide existed at the electrode surface was used as the first electrode 21 (anode). Specifically, an electrode (JP-330) manufactured by De Nora Permelec Ltd. was used. With the exception of the anode, the remaining portions of the electrode pair had the same configuration as the electrode pair of Example 1.

Figure 12:
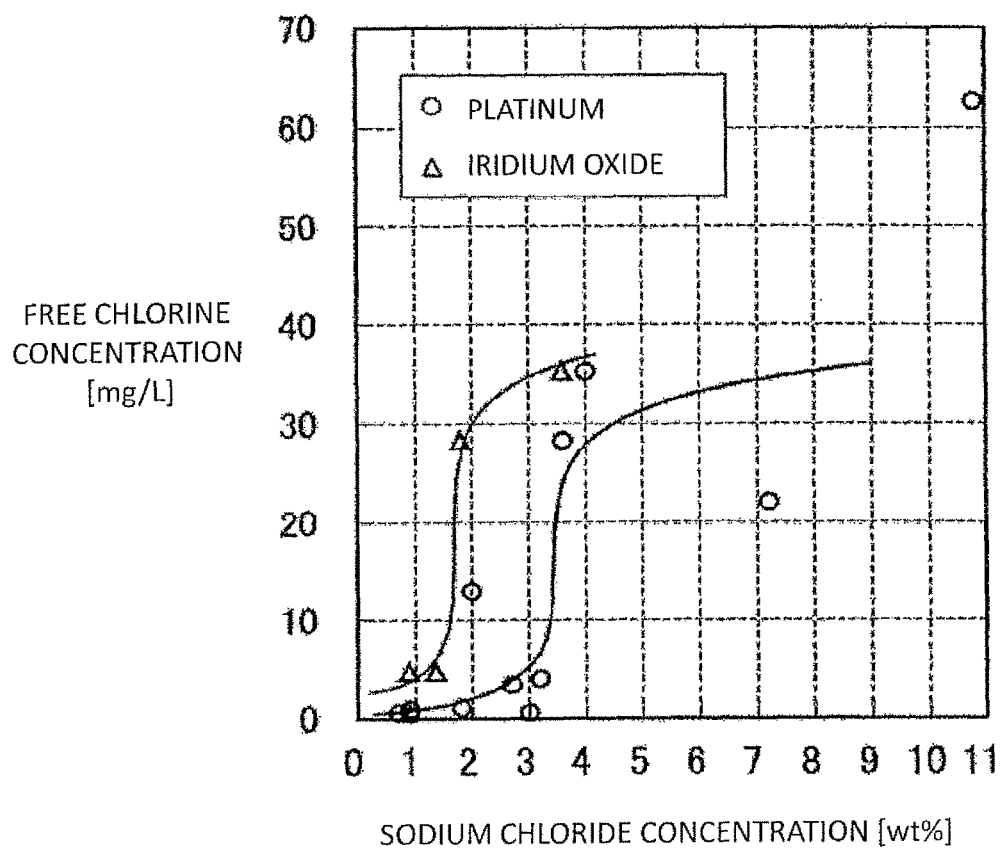
FIG. 12 is a graph illustrating test results from Example 5.

The results of Example 5 are illustrated in FIG. 12. In FIG. 12, the results of Example 4 are also shown for the purpose of comparison. As illustrated in FIG. 12, in Example 5 which used the electrode in which iridium oxide existed at the surface, the concentration of free chlorine decreased greatly when the sodium chloride concentration was lower than about 1.5 wt %. On the other hand, in Example 4 which used the electrode in which platinum existed at the surface, the concentration of free chlorine decreased greatly when the sodium chloride concentration was lower than about 3.4 wt %. These results indicate that by using an electrode in which platinum exists at the surface as the anode, the concentration of free chlorine can be reduced efficiently in aqueous solutions having a broad range of salt concentrations.

Example 6

In Example 6, a flow-type electrolytic cell similar to the electrolytic cell 211 illustrated in FIG. 4 was used, and tests were conducted to increase and decrease the concentration of free chlorine. For the electrode pair, the same electrode pair as that used in Example 1 was used.

For the aqueous solution, an aqueous solution of sodium chloride (physiological saline solution) with a concentration of 0.9 wt % was used, and 200 mL of this aqueous solution was circulated through a circulation passage including the electrolytic cell. Process (i) and (ii) were performed in this state. In process (i), a voltage was applied for 4 minutes so that a constant current of 2 A flowed between the first electrode 21 (anode) and the second electrode 22 (cathode). This voltage application caused the concentration of free chlorine in the aqueous solution to reach about 200 mg/L. In the subsequent process (ii), a voltage of 1.2 V was applied for 60 minutes between the first electrode 21 (anode) and the second electrode 22 (cathode).

Figure 13:
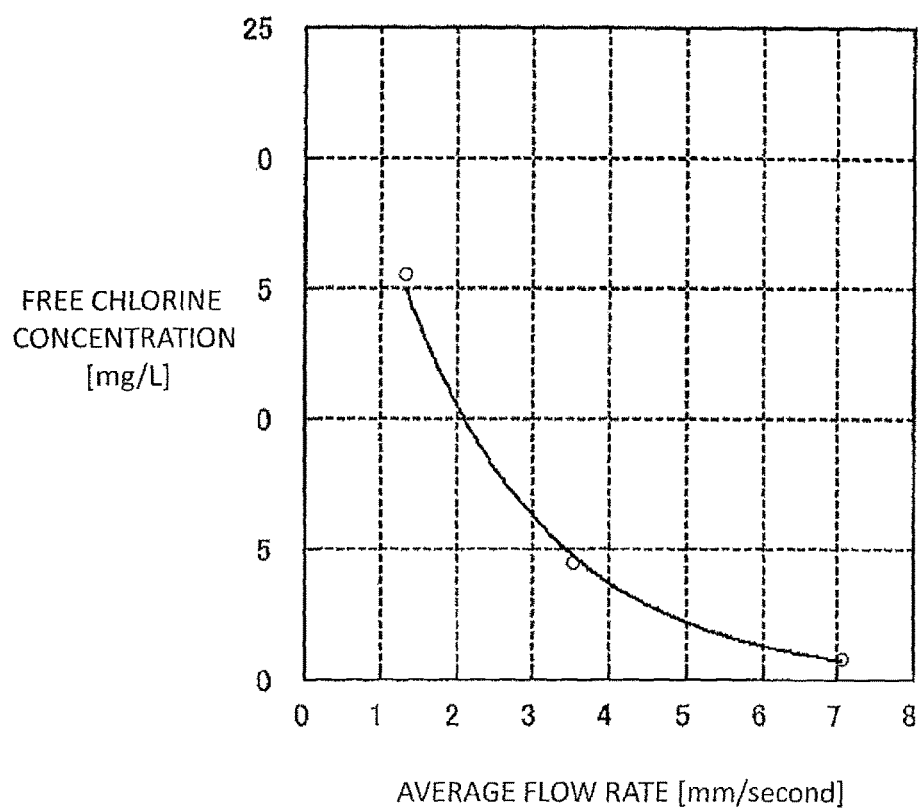
FIG. 13 is a graph illustrating test results from Example 6.

In Example 6, processes (i) and (ii) were performed with the average flow volume of the aqueous solution through the inside of the electrolytic cell set to 150 mL/minute, 400 mL/minute and 800 mL/minute. Conversion of these flow volumes to average flow rates inside the electrolytic cell yields corresponding flow rates of 1.3 mm/s, 3.5 mm/s and 7.1 mm/s respectively. The concentration of free chlorine after the voltage application of process (ii) is illustrated in FIG. 13. As illustrated in FIG. 13, a tendency was observed for a greater reduction in the concentration of free chlorine when the flow rate was faster. Specifically, the concentration of free chlorine decreased greatly when the flow rate was 3.5 mm/s or more.

Example 7

Example 7 describes an example in which the surface area of the second cathode was set to a larger value than the surface area of the first cathode. The configuration of the electrode unit 140 used in Example 7 is illustrated schematically in FIG. 14. Further, the electrolytic cell used in Example 7 is illustrated schematically in FIG. 15.

Figure 14:
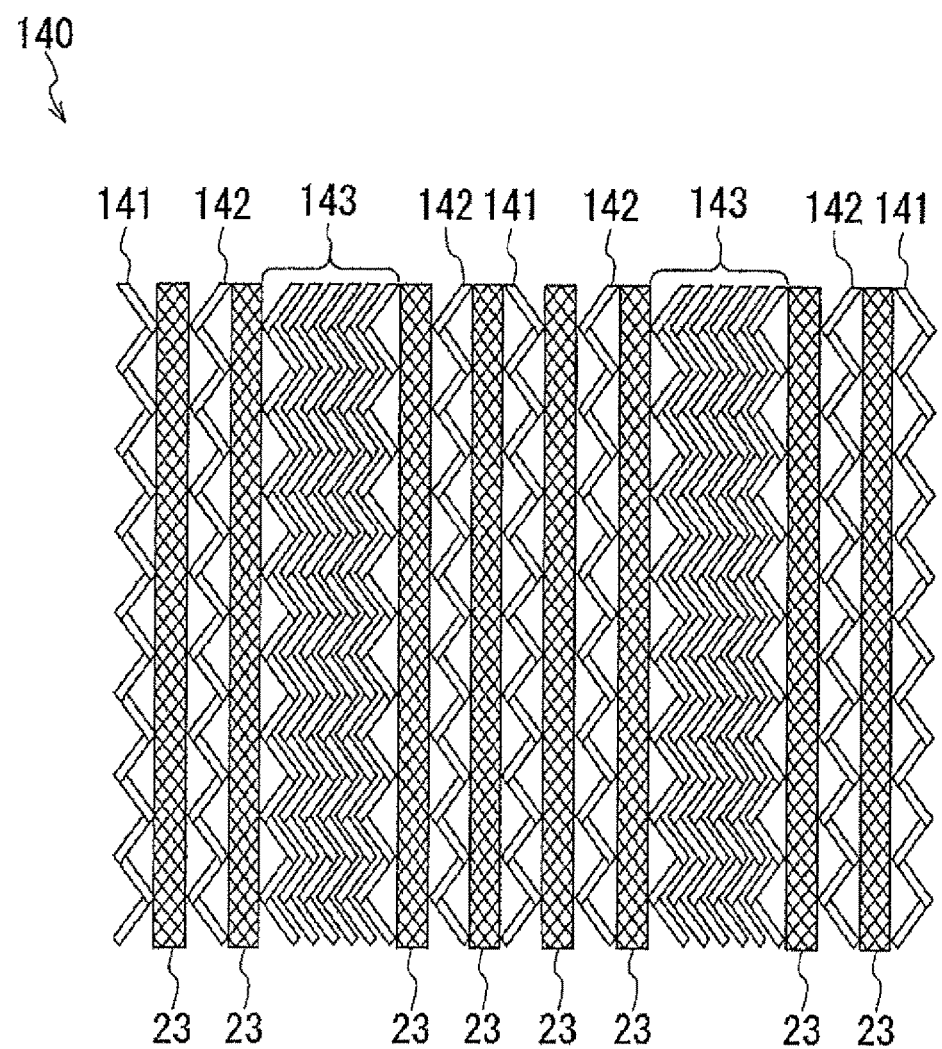
FIG. 14 is a diagram schematically illustrating the structure of one example of an electrode unit used in Example 7.

The electrode unit 140 of FIG. 14 includes a first electrode 141, a second electrode 142, a third electrode 143 and spacers 23. The first to third electrodes 141 to 143 are each composed of the same types of net-like electrodes. However, the number of net-like electrodes within each of the electrodes differs. The first electrode 141 was formed of 3 net-like electrodes. The second electrode 142 was formed of 4 net-like electrodes. The third electrode 143 was formed of 22 net-like electrodes. In FIG. 14 and FIG. 15, in order to simplify the illustrations, the number of net-like electrodes constituting the third electrode 143 has been reduced. For each net-like electrode, a platinum-coated electrode having a size of 80 mm×60 mm and a thickness of 0.5 mm was used. Each spacer used a resin net-like spacer having a size of 80 min×60 mm and a thickness of 0.5 mm.

As illustrated in FIG. 15, the electrode unit 140 was positioned inside the cell 211 so that each of the net-like electrodes was parallel to the flow direction of the aqueous solution. A circulation passage including the inlet 211a and the outlet 211b was formed, and 1.5 L of saline solution was circulated through this circulation passage. For the saline solution, a solution having a concentration of free chlorine of about 240 to 250 ppm (about 240 to 250 mg/L) and a concentration of NaCl of 0.65 wt % was used. The flow volume of the saline solution through the circulation passage was set to 0.3 L/minute. Process (ii) was performed in a state where the saline solution was being circulated.

In Example 7, process (ii) was performed with various values for the ratio between the surface area of the second anode and the surface area of the second cathode. The electrode surface area ratio in each of the tests is shown in Table 3.

TABLE 3

| | Number of net-like electrodes | | Surface area ratio |
|---|---|---|---|
| | Second cathode | Second anode | second cathode/second anode |
| Test 7-1 | 26 | 3 | 26/3 |
| Test 7-2 | 16 | 3 | 16/3 |
| Test 7-3 | 4 | 3 | 4/3 |

In Test 7-1, the first electrode 141 of the electrode unit 140 was used as the second anode, and the second electrode 142 and third electrode 143 were used as the second cathode. In this case, (surface area of second cathode)/(surface area of second anode)=26/3. In other words, the surface area of the second cathode was about 9 times that of the surface area of the second cathode. In Test 7-3, the first electrode 141 was used as the second anode, the second electrode 142 was used as the second cathode, and no voltage was applied to the third electrode 143. In Test 7-2, with the exception of altering the number of net-like electrodes that constitute the third electrode 143 of the electrode unit 140 to 12, testing was performed in the same manner as Test 7-1. In Test 7-2, the electrode unit was thinner as a result of reducing the number of net-like electrodes that constitute the third electrode 143, thus generating space inside the cell 211. In Test 7-2, in order to prevent the flow of the saline solution from becoming concentrated in that space, a spacer 23 was positioned in that space.

Figure 16:
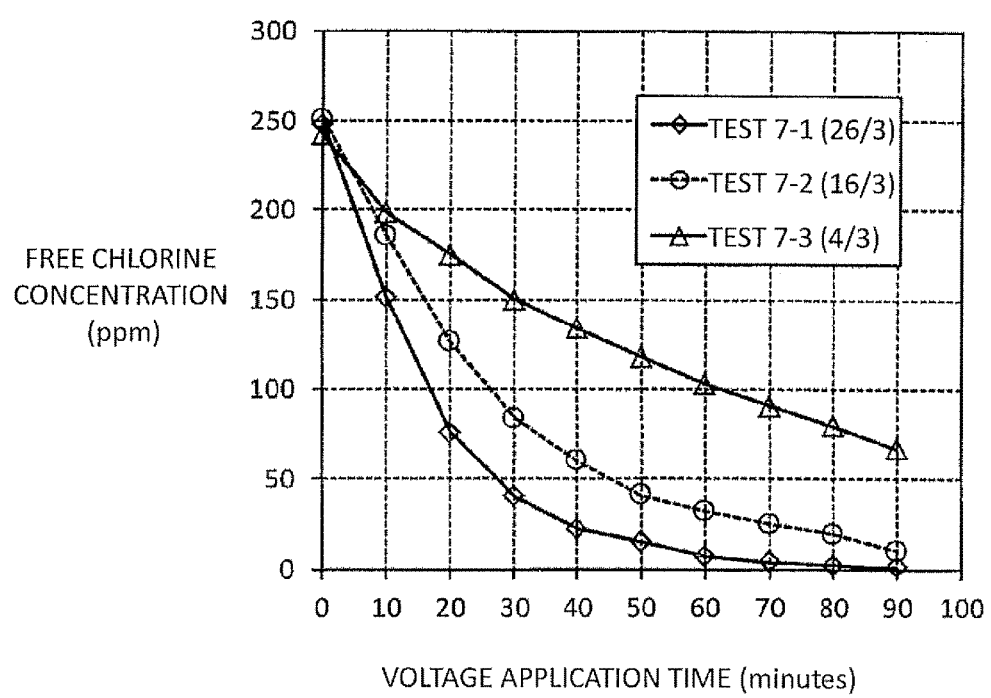
FIG. 16 is a graph illustrating results from Example 7.

The changes in the concentration of free chlorine observed in Tests 7-1 to 7-3 are illustrated in FIG. 16. As illustrated in FIG. 16, the more the value of (surface area of second cathode)/(surface area of second anode) was increased, the faster the rate of reduction in the concentration of free chlorine became. When process (i) is performed using the electrode unit including the third electrode 143, process (i) may be conducted without applying a voltage to the third electrode 143. For example, process (i) may be performed using the first electrode 141 as the first anode and the second electrode 142 as the first cathode.

Example 8

In Example 8, process (i) and process (ii) were performed, and the change in the concentration of free chlorine was measured. In process (ii) of Example 8, the voltage applied between the electrodes was reduced in a stepwise manner. In Example 8, the same electrode unit and circulation passage as those used in Test 7-1 of Example 7 were used. A saline solution having a concentration of NaCl of 0.65 wt % was circulated through the circulation passage, and processes (i) and (ii) were performed in that state.

Figure 17A:
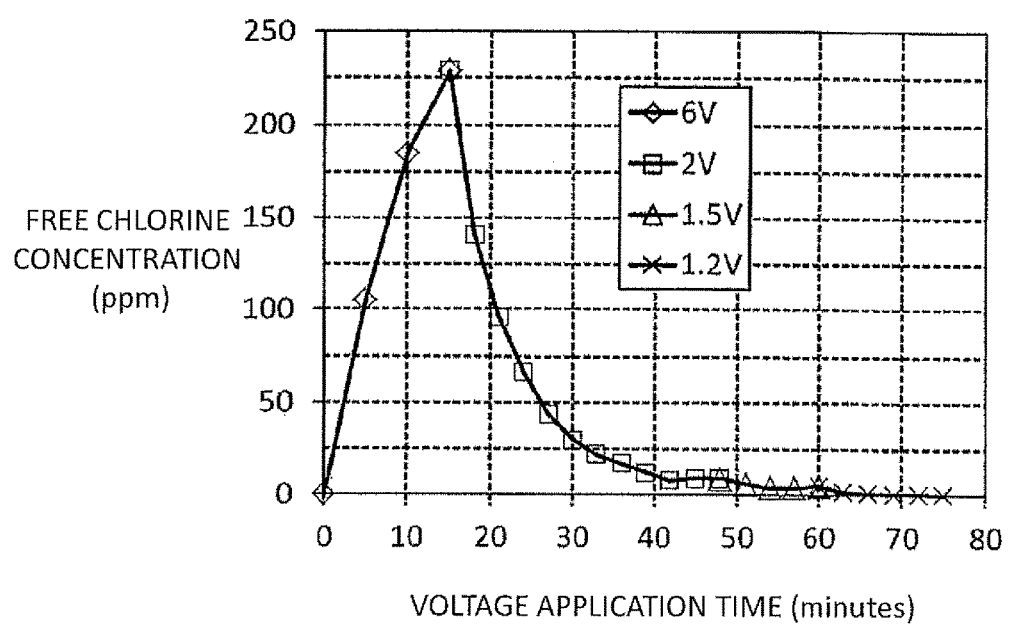
FIG. 17A is a graph illustrating results from Example 8.
Figure 17B:
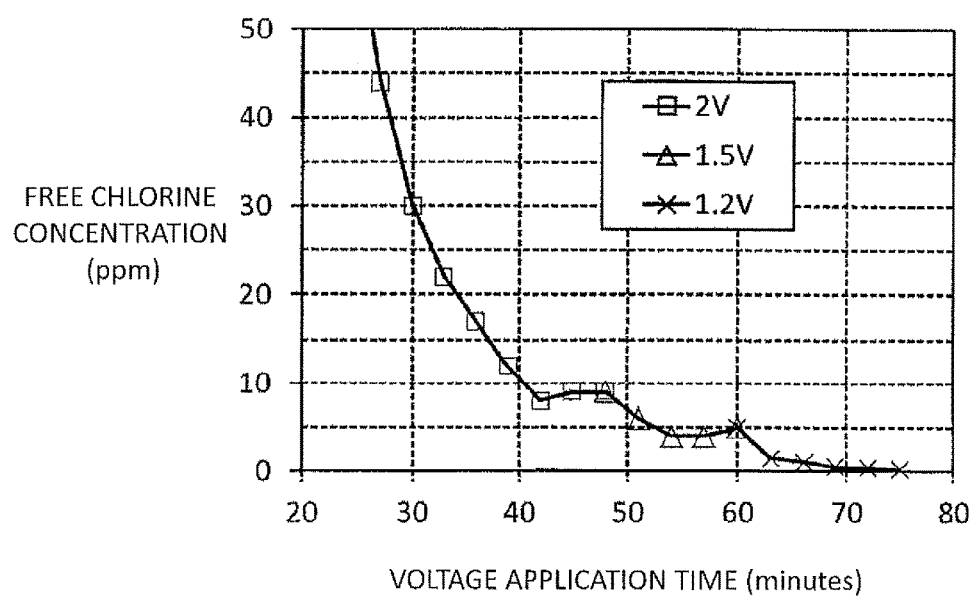
FIG. 17B is a partial enlargement of the graph illustrated in FIG. 17A.

In process (i), a DC voltage of 6 V was applied between the first anode and the first cathode. In process (ii), the magnitude of the DC voltage applied between the second anode and the second cathode was initially set to 2 V, and was subsequently reduced to 1.5 V, and then to 1.2 V. The change in the concentration of free chlorine is illustrated in FIG. 17A. A partial enlargement of FIG. 17A is shown in FIG. 17B.

In process (i) when a DC voltage of 6 V was applied between the electrodes, as illustrated in FIG. 17A, the concentration of free chlorine increased. When process (ii) was initiated by applying a DC voltage of 2 V between the electrodes, then as illustrated in FIG. 17A, the concentration of free chlorine decreased. However, when the DC voltage application of 2 V was continued, as illustrated in FIG. 17B, the concentration of free chlorine did not decrease below 8 to 9 ppm. When the applied voltage was then altered to 1.5 V, the concentration of free chlorine decreased once again. However, when the DC voltage application of 1.5 V was continued, as illustrated in FIG. 17B, the concentration of free chlorine did not decrease below 4 to 5 ppm. When the applied voltage was then altered to 1.2 V, the concentration of free chlorine decreased once again. The final concentration of free chlorine was able to be reduced to 1 ppm or less. In this manner, by reducing the applied voltage in process (ii) in a stepwise manner, the concentration of free chlorine was able to be reduced to an extremely low level in a short period of time.

When process (i) was performed with an applied voltage of 4 V, using the same apparatus as that used in Example 8, the concentration of free chlorine in the saline solution increased.

INDUSTRIAL APPLICABILITY

The present invention can be used in a method and apparatus for controlling the concentration of free chlorine, and can also be used in a sterilization method and sterilization apparatus using said method and apparatus.

REFERENCE SIGNS LIST 11, 211: Cell
12: Power source
13: Controller
14: Pump
20: Electrode pair
21, 141: First electrode
22, 142: Second electrode
143: Third electrode
23: Spacer
30: Aqueous solution
100, 200: Apparatus
300: Sterilization target
301: Circulation passage

The invention claimed is:

1. A method for controlling concentration of free chlorine using a plurality of electrodes, the method comprising, in order:
(i) adjusting a potential of a first anode and a potential of a first cathode in an aqueous solution comprising chloride ions, thereby increasing a concentration of free chlorine in the aqueous solution, and
(ii) adjusting a potential of a second anode and a potential of a second cathode in the aqueous solution, thereby decreasing a concentration of free chlorine in the aqueous solution, wherein
a difference between the potential of the second anode and the potential of the second cathode in a process of (ii) is smaller than a difference between the potential of the first anode and the potential of the first cathode in a process of (i),
the first anode and the first cathode are composed of one portion and one other portion of the plurality of electrodes, respectively, and
the second anode and the second cathode are composed of one portion and one other portion of the plurality of electrodes, respectively.

2. The method according to claim 1, wherein
a DC voltage of at least 4 V is applied between the first anode and the first cathode in the process of (i), and
a DC voltage within a range from 0.6 V to 3 V is applied between the second anode and the second cathode in the process of (ii).

3. The method according to claim 2, wherein
the first anode, the first cathode, the second anode and the second cathode are each an electrode in which platinum exists at a surface of the electrode.

4. The method according to claim 1, wherein
a surface area of the second cathode is larger than a surface area of the first cathode, and
a surface area of the second cathode is larger than a surface area of the second anode.

5. The method according to claim 4, wherein
the plurality of electrodes comprises a first electrode used as the first anode, a second electrode used as the first cathode, and a third electrode,
a voltage is not applied to the third electrode in the process of (i), and
the third electrode is used as at least a portion of the second cathode in the process of (ii).

6. The method according to claim 1, further comprising, either between the process of (i) and the process of (ii), or after the process of (ii):

(x) adjusting a potential of a third anode and a potential of a third cathode in the aqueous solution, thereby maintaining a concentration of free chlorine in the aqueous solution within a fixed range, wherein
the third anode and the third cathode are composed of one portion and one other portion of the plurality of electrodes, respectively.

7. The method according to claim 1, wherein
during the process of (ii), a difference between a potential of the second anode and a potential of the second cathode is reduced gradually.

8. A sterilization method for performing sterilization using an aqueous solution comprising free chlorine, the sterilization method comprising:
the method according to claim 1, and
(I) sterilizing a sterilization target using the aqueous solution treated by the process of (i).

9. The sterilization method according to claim 8, further comprising, after a process of (I):
(II) washing the sterilization target using the aqueous solution treated by the process of (ii).

10. The sterilization method according to claim 8, wherein
adjustment of the potentials in the process of (i) and the process of (ii) is performed within an electrolytic cell, and
the process of (i) and the process of (ii) are performed in a state where the aqueous solution is circulated between the electrolytic cell and the sterilization target.

11. An apparatus for controlling concentration of free chlorine, the apparatus comprising:
a plurality of electrodes,
a power source for applying a voltage to the plurality of electrodes, and
a controller for controlling the power source, wherein
the controller executes, in order:
(i) adjusting a potential of a first anode and a potential of a first cathode in an aqueous solution comprising chloride ions, thereby increasing a concentration of free chlorine in the aqueous solution, and
(ii) adjusting a potential of a second anode and a potential of a second cathode in the aqueous solution, thereby decreasing a concentration of free chlorine in the aqueous solution,
a difference between a potential of the second anode and a potential of the second cathode in a process of (ii) is smaller than a difference between a potential of the first anode and a potential of the first cathode in a process of (i),
the first anode and the first cathode are composed of one portion and one other portion of the plurality of electrodes, respectively, and
the second anode and the second cathode are composed of one portion and one other portion of the plurality of electrodes, respectively.

12. The apparatus according to claim 11, wherein
a DC voltage of at least 4 V is applied between the first anode and the first cathode in the process of (i), and
a DC voltage within a range from 0.6 V to 3 V is applied between the second anode and the second cathode in the process of (ii).

13. The apparatus according to claim 12, wherein
the first anode, the first cathode, the second anode and the second cathode are each an electrode in which platinum exists at a surface of the electrode.

14. The apparatus according to claim 11, wherein
a surface area of the second cathode is larger than a surface area of the first cathode, and
a surface area of the second cathode is larger than a surface area of the second anode.

15. The apparatus according to claim 14, wherein
the plurality of electrodes comprises a first electrode used as the first anode, a second electrode used as the first cathode, and a third electrode,
a voltage is not applied to the third electrode in the process of (i), and
the third electrode is used as at least a portion of the second cathode in the process of (ii).

16. The apparatus according to claim 11, wherein either between the process of (i) and the process of (ii), or after the process of (ii), the controller executes:
(x) adjusting a potential of a third anode and a potential of a third cathode in the aqueous solution, thereby maintaining a concentration of free chlorine in the aqueous solution within a fixed range, wherein
the third anode and the third cathode are composed of one portion and one other portion of the plurality of electrodes, respectively.

17. The apparatus according to claim 11, wherein
during the process of (ii), the controller gradually reduces a difference between a potential of the second anode and a potential of the second cathode.

18. A sterilization apparatus for performing sterilization using an aqueous solution comprising free chlorine, wherein
the sterilization apparatus comprises the apparatus according to claim 11, and
the controller executes (I) sterilizing a sterilization target using the aqueous solution treated by the process of (i).

19. The sterilization apparatus according to claim 18, wherein after a process of (I), the controller executes:
(II) washing the sterilization target using the aqueous solution treated by the process of (ii).

20. The sterilization apparatus according to claim 18, comprising an electrolytic cell in which application of the voltage is performed in the process of (i) and the process of (ii), wherein
the process of (i) and the process of (ii) are performed in a state where the aqueous solution is circulated between the electrolytic cell and the sterilization target.

* * * * *